United States Patent
Daftary et al.

(10) Patent No.: US 12,128,222 B2
(45) Date of Patent: Oct. 29, 2024

(54) SAFETY HOUSING BASED IMPLANT/MEDICAMENT INJECTING SYSTEM

(71) Applicant: BHARAT SERUMS AND VACCINES LTD, Maharashtra (IN)

(72) Inventors: Gautam Vinod Daftary, Mumbai (IN); Suresh Kumar Natarajan, Bangalore (IN); Vasanthan Mani, Bangalore (IN); Cyril Fernandez Lourdnathan Joseph, Wayanad (IN); Sangeeta Hanurmesh Rivankar, Mumbai (IN)

(73) Assignee: BHARAT SERUMS AND VACCINES LTD, Mumbai (IN)

( * ) Notice: Subject to any disclaimer, the term of this patent is extended or adjusted under 35 U.S.C. 154(b) by 161 days.

(21) Appl. No.: 17/583,965

(22) Filed: Jan. 25, 2022

(65) Prior Publication Data
US 2022/0203042 A1 Jun. 30, 2022

Related U.S. Application Data

(62) Division of application No. 16/322,974, filed as application No. PCT/IN2016/000238 on Oct. 3, 2016, now Pat. No. 11,273,266.

(30) Foreign Application Priority Data

Aug. 5, 2016 (IN) .............................. 201621026847

(51) Int. Cl.
*A61M 5/32* (2006.01)
*A61M 5/315* (2006.01)
(Continued)

(52) U.S. Cl.
CPC ...... *A61M 5/3221* (2013.01); *A61M 5/31501* (2013.01); *A61M 5/31531* (2013.01);
(Continued)

(58) Field of Classification Search
CPC .............. A61M 5/178; A61M 5/31511; A61M 5/31515; A61M 5/31578; A61M 5/3158;
(Continued)

(56) References Cited

U.S. PATENT DOCUMENTS

| 4,747,829 A | 5/1988 | Jacob et al. |
| 4,969,877 A | 11/1990 | Kornberg |

(Continued)

FOREIGN PATENT DOCUMENTS

| EP | 0966983 | 12/1999 |
| WO | 2012/098356 | 7/2012 |

OTHER PUBLICATIONS

International Search Report issued in PCT/IN2016/000238 on May 23, 2017 (5 pages).

*Primary Examiner* — Kami A Bosworth
(74) *Attorney, Agent, or Firm* — MASUVALLEY & PARTNERS; Peter Martinez

(57) ABSTRACT

A safety housing based implant/medicament injecting system. The system includes a needle assembly prefilled with an implant/medicament for injection and an injecting needle/cannula, a housing for accommodating the needle assembly under usual bias inside said housing, a plunger means having a plunger rod configured for stage-wise forward motion including an initial-injecting plunger forward motion with the needle assembly within the housing to first engage the needle assembly with the housing and a subsequent continuing-injecting plunger forward motion independent of the needle assembly for injecting the implant/medicament. The needle assembly configured to return post-injecting to be secured inside said housing blocking any subsequent use thereof.

13 Claims, 20 Drawing Sheets

(51) Int. Cl.
*A61M 5/50* (2006.01)
*A61M 37/00* (2006.01)

(52) U.S. Cl.
CPC ........ *A61M 5/3234* (2013.01); *A61M 5/3243* (2013.01); *A61M 5/50* (2013.01); *A61M 37/0069* (2013.01); *A61M 2005/31508* (2013.01); *A61M 2005/3223* (2013.01); *A61M 2005/3231* (2013.01); *A61M 2005/3258* (2013.01); *A61M 2005/3261* (2013.01); *A61M 2005/3267* (2013.01); *A61M 2205/273* (2013.01); *A61M 2205/581* (2013.01)

(58) Field of Classification Search
CPC ........ A61M 5/31591; A61M 2005/206; A61M 37/0069
See application file for complete search history.

(56) References Cited

U.S. PATENT DOCUMENTS

| | | | |
|---|---|---|---|
| 5,201,719 | A | 4/1993 | Collins et al. |
| 5,273,532 | A | 12/1993 | Niezink et al. |
| 6,102,896 | A | 8/2000 | Roser |
| 7,118,552 | B2 | 10/2006 | Shaw et al. |
| 8,029,458 | B2 | 10/2011 | Cherif-Cheikh et al. |
| 2002/0010421 | A1 | 1/2002 | Buttgen et al. |
| 2002/0111603 | A1 | 8/2002 | Cheikh |
| 2003/0004457 | A1 | 1/2003 | Andersson |
| 2007/0129686 | A1 | 6/2007 | Daily et al. |
| 2008/0221529 | A1 | 9/2008 | Kiehne |
| 2012/0253314 | A1 | 10/2012 | Harish et al. |
| 2014/0018725 | A1 | 1/2014 | Potter et al. |
| 2019/0117903 | A1 | 4/2019 | Rathore et al. |

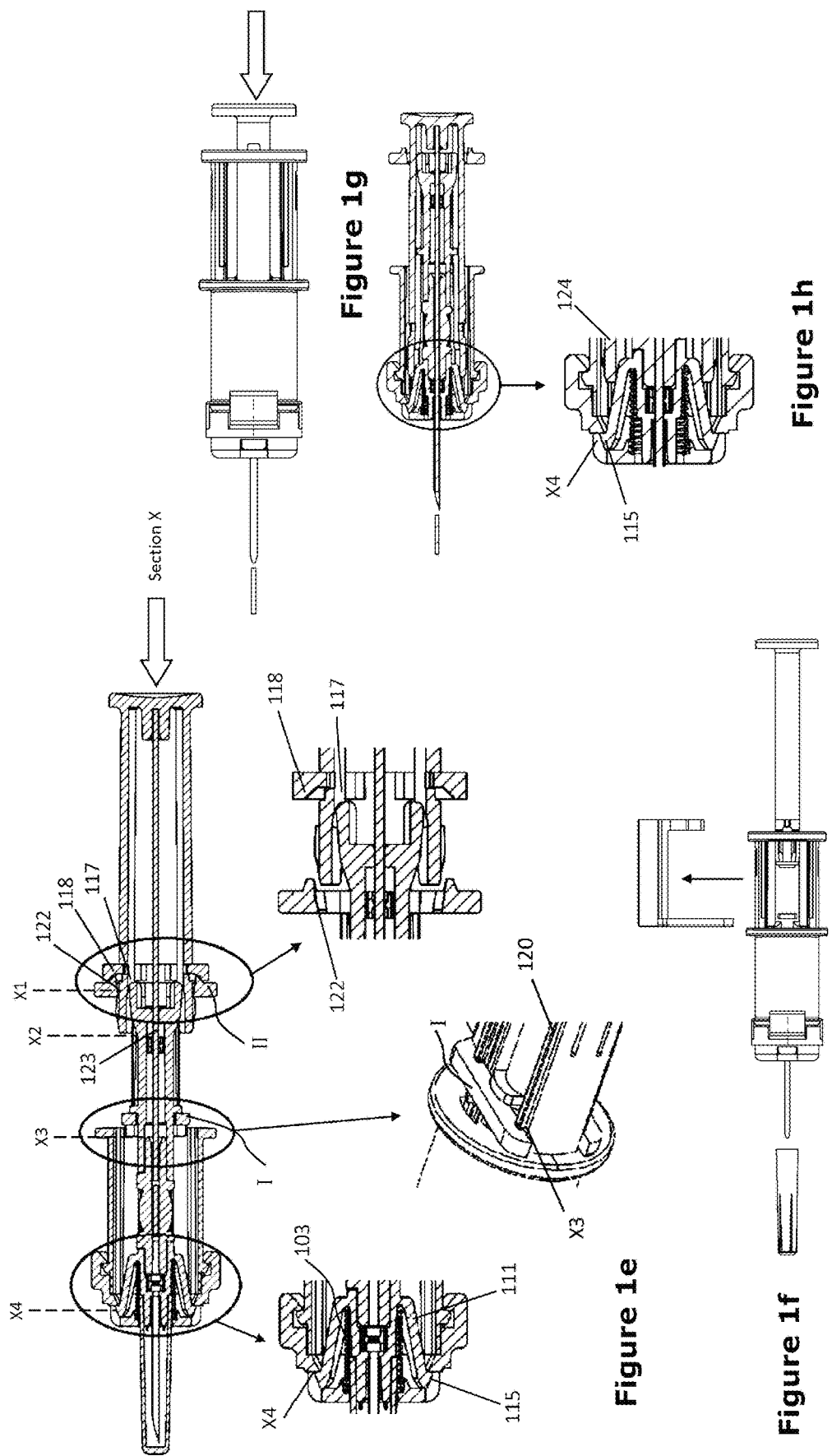

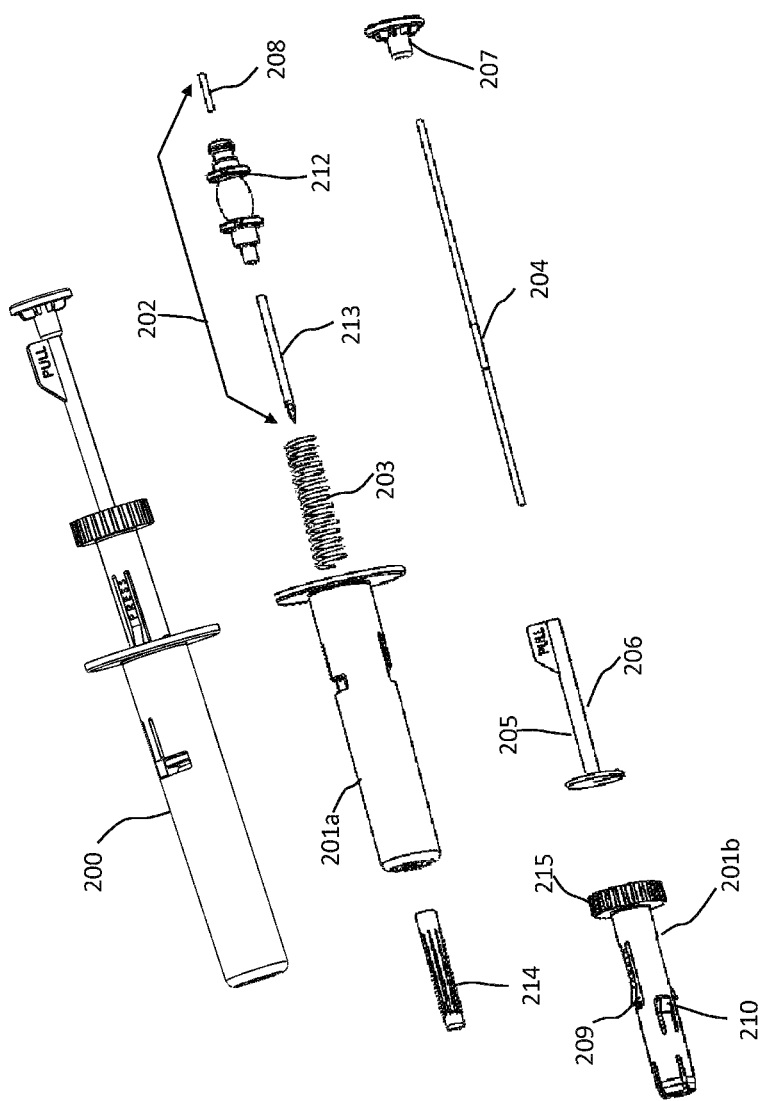
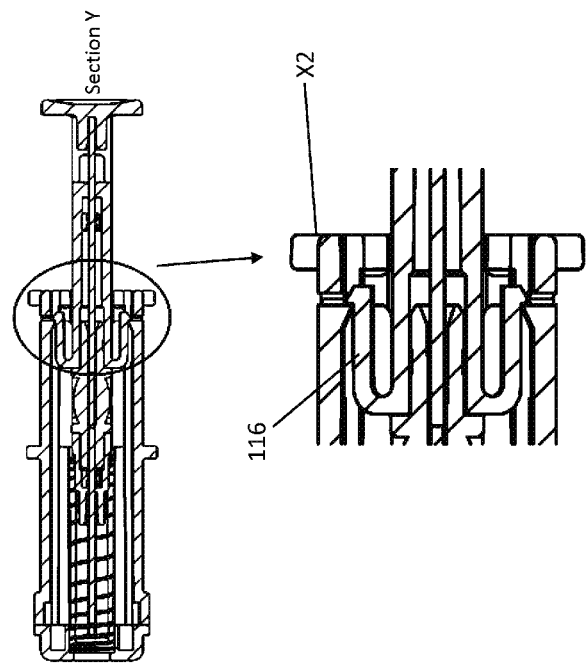
Figure 2a
Figure 1i

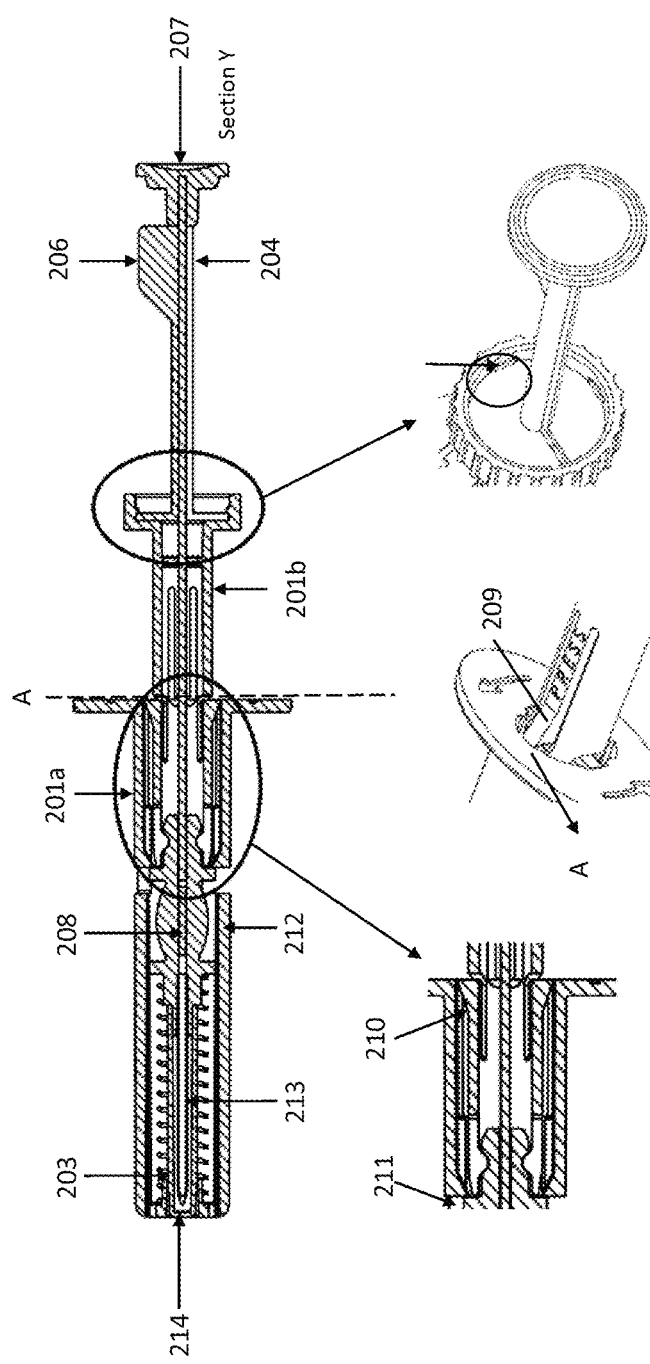
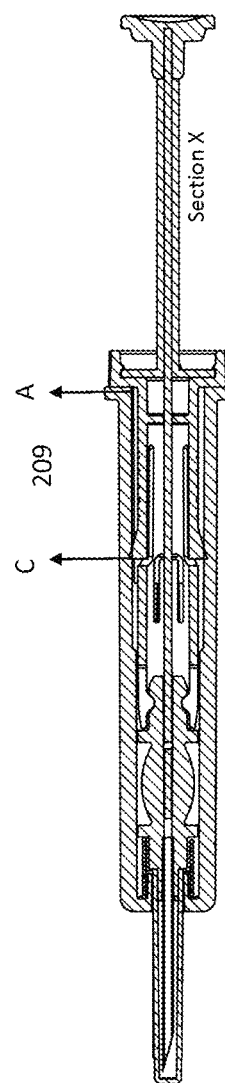
Figure 2c
Figure 2d

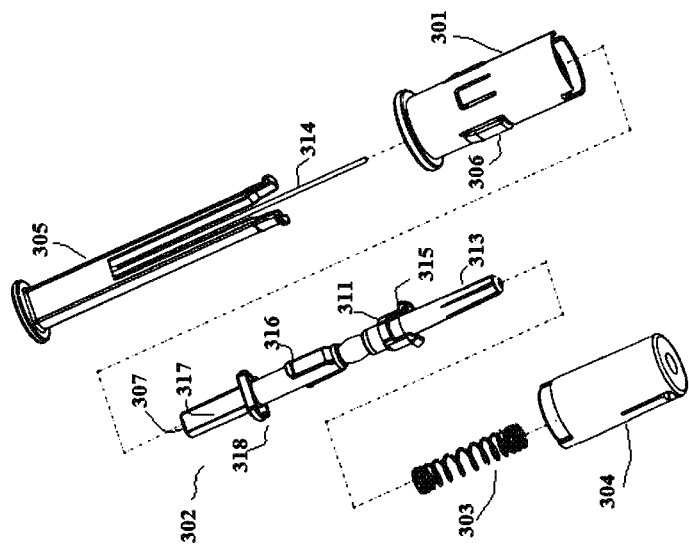
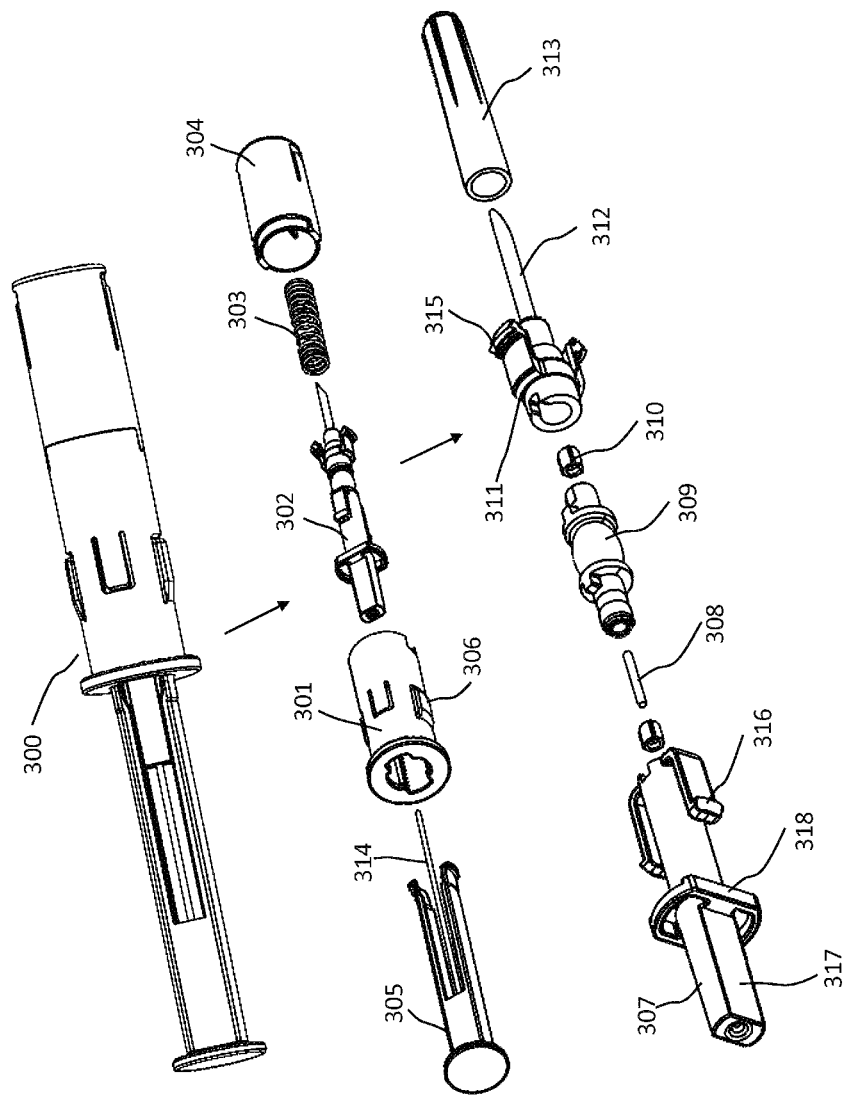
Figure 3b
Figure 3a

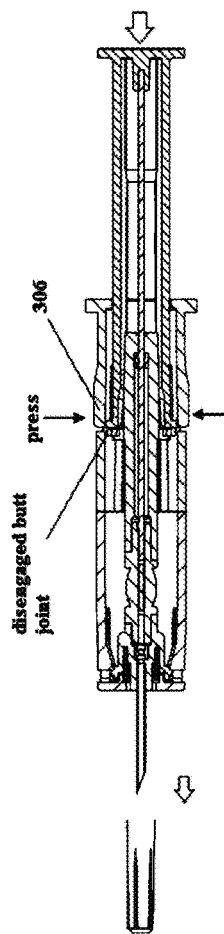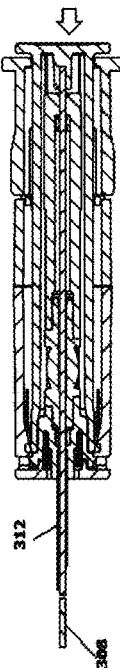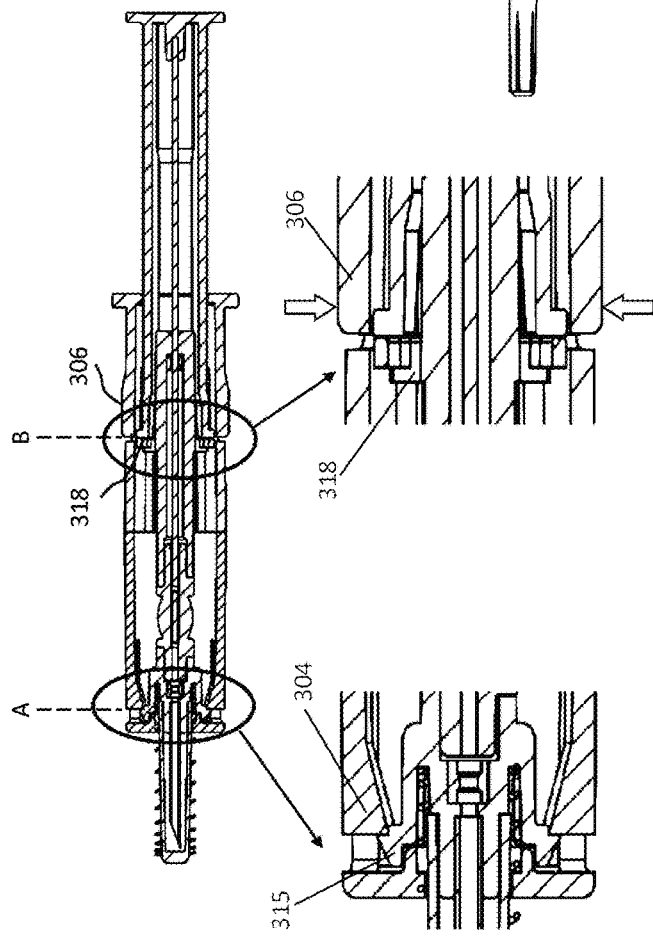

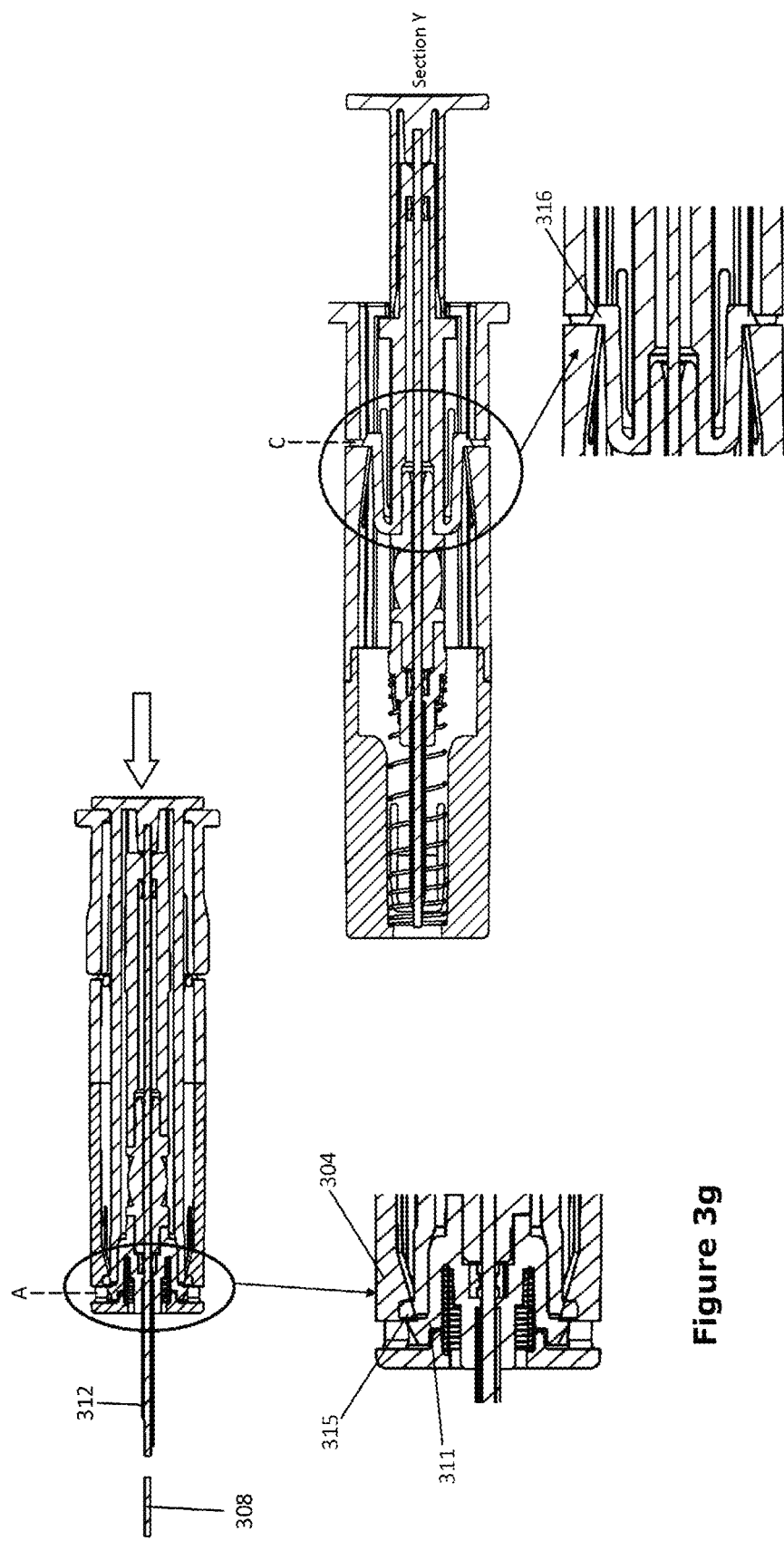

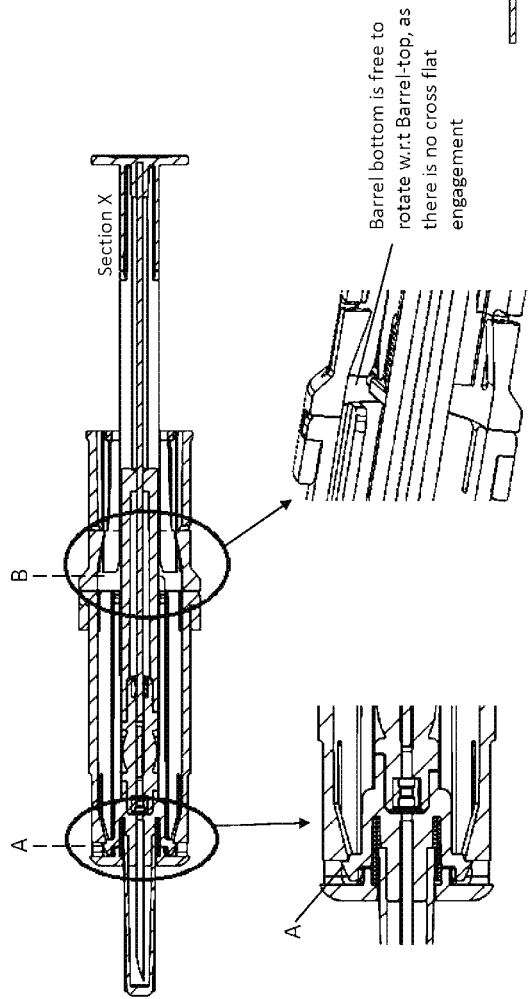
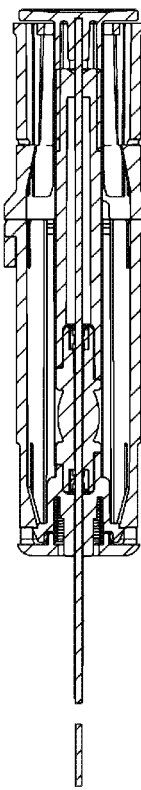
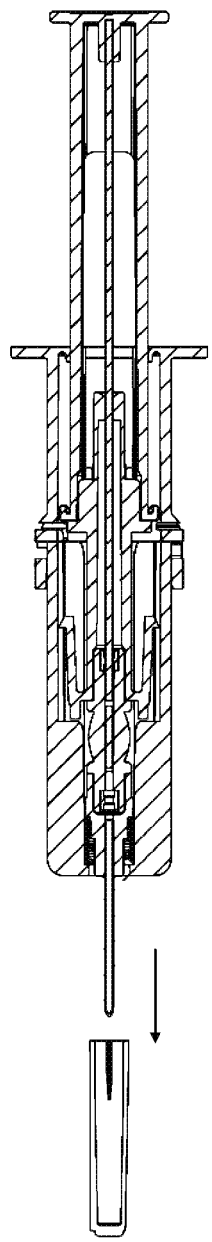
Figure 4e
Figure 4f
Figure 4g

SAFETY HOUSING BASED IMPLANT/MEDICAMENT INJECTING SYSTEM

RELATED APPLICATIONS

This application is a divisional of and claims priority to U.S. patent application Ser. No. 16/322,974, filed Feb. 4, 2019, which is a U.S. National Phase application under 35 U.S.C. § 371 of International Patent Application No. PCT/IN2016/000238, International Filing Date Oct. 3, 2016, which claims the benefit of India Patent Application No. 201621026847 filed Aug. 5, 2016; all of which are incorporated herein by reference in their entireties.

FILED OF THE INVENTION

The present invention relates to a system for safely injecting substances into body/tissue of human/animal. More particularly, the present invention is directed to provide a prefilled medicament injecting system with a safety housing for safely injecting substances like medicament/implant into the body or tissue of the human or the animal. The safety housing is specially configured to prevent any contact between injecting needle and the user during the injecting procedure or in the post injecting stage.

BACKGROUND ART

A conventional medicament/implant injecting system includes an injecting syringe, which is filled with a selected dosage of the medicament/implant for distribution to the end use. The injecting system further includes a sharp-pointed element or injecting needle at front of the injecting syringe for piercing into the body/tissue and delivering the medicament of the injecting syringe.

Sometimes, the injecting needle of the injecting system causes needle stick injuries to the user who is using the injecting system to inject the medicament.

The needle stick injuries are common to the healthcare professionals and, in some cases, the needle stick injuries exposed the healthcare professionals to contamination from infected patients being injected.

In recent times, different safety shields for injecting systems have been reported in the art to avoid the needle stick injuries. These safety shields are adapted to move in axial direction with respect to the injecting syringe to expose the needle 'for use' only during injection of the medicament/implant. E.g.

EP 0966983 A1 discloses a shield system and a syringe which is coupled to the shield system. The shield system includes an outer syringe holder and an inner shield. The syringe is inserted within the enclosure defined by the outer holder and inner shield. When sufficient pressure is exerted on the holder by the syringe barrel, the shield is released and is urged in a distal direction by a spring located between the barrel and shield, putting the shield in an extended position and covering the needle.

U.S. Pat. No. 8,029,458 B2 discloses a device for the injection of a solid or semi-solid implant comprising of a main hollow body having a hollow needle fixed thereto, into which the implant is introduced; a secondary body which is disposed coaxially inside the main body and which surrounds the needle and a plunger rod which can slide coaxially inside the hollow needle. The injection device is arranged such that: (i) when it is pressed against the tissues, the main body slides along the length of the secondary body from a proximal position to a distal position such that the needle can penetrate the tissues, whereby the movement of the main body is accompanied by the concomitant movement of the plunger rod; and (ii) the plunger rod remains fixed and maintains the implant at the required depth in the tissues until the needle is removed therefrom when the main body is returned from the distal position to the proximal position.

U.S. Pat. No. 7,118,552 B2 discloses an automatically operable safety shield system for syringes which includes an inner holder into which the syringe may be inserted, an outer shield mounted outwards from the inner holder being biased with a spring and axially movable relative to the inner holder between retracted and extended positions wherein in the retracted position of the outer shield the syringe needle is exposed for use. The inner holder comprises at least one first opening and the outer shield comprises at least one first stop member, the first stop member being engageable with the first opening when the outer shield is in the retracted position, the inner holder having distal to the first opening at least one first indentation, the first stop member being engageable with the first indentation when the outer shield is in the extended position. A trigger is positioned within the inner holder and axially movable relative to said inner holder such that it can contact the first stop member when it is engaged with the first opening and disengage the first stop member from the first opening, allowing the spring to move the outer shield to the extended position.

Safety shield systems or the safety housings for injecting system such as mentioned in both the U.S. Pat. No. 8,029,458 B2 and U.S. Pat. No. 7,118,552 B2 include an inner housing to enclose the injecting syringes and an outer housing to accommodate the inner housing wherein the outer housing moves to expose the injecting syringes and goes back to its original position post injection. Now this two part housing structures based covering and selective exposure of the injecting syringe with the assistance of a trigger mechanism makes the whole arrangement complex and difficult to use, for health professional as the outer hosing needs to be moved separately before injecting and thus continuing to expose the user to accidental hazards.

The above state of art clearly indicates that, there has been a need for developing a simple, easy-to-use, safety housing for injecting system which can prevent any contact between injecting needle and the user during the injecting procedure or in the post injecting stage to avoid the needle stick injuries.

OBJECTS OF THE INVENTION

The basic object of the present invention is to develop a simple, user friendly safety shield system or the safety housing for medicament/implant injecting system which would expose the injecting needle, only during injecting procedure and automatically enclose the injecting needle in post injection stage such as to avoid the needle stick injuries.

Another object of the present invention is to develop a safety housing for medicament/implant injecting system which will be adapted to permanently enclose injecting unit post use for restricting any further use of the injecting unit and/or accidental exposure of the used needle.

SUMMARY OF THE INVENTION

In above mentioned push type safety housing based implant/medicament injecting system, the positive lock includes at least one opening or slot in the plunger externally at a front end; and at least one cooperative protrusion on the second end of the safety clip configured to be detachably engaged with said at least one opening or slot in the plunger.

In above mentioned push type safety housing based implant/medicament injecting system, the first end of the safety clip is coupled with the housing by a tongue and groove joint facilitating sliding of the safety clip through the housing;

said first end of the safety clip is coupled with the label holder by a butt joint ensuring that pushing force applied on the plunger gets transferred to the needle assembly via the safety clip and enabling cooperative forward movement of the plunger and the needle assembly inside the housing; and said cooperative forward movement of the plunger and the needle assembly restricts plunger rod movement through the plunger rod guide and thus prevent movement of the implant/medicament independently with respect to the needle assembly during driving of the needle assembly.

In above mentioned push type safety housing based implant/medicament injecting system, the first engagement means comprises a snap lock on the needle hub configured to engage with cooperative locking portion in the housing cap when the cannula and protective cap are completely ejected out from the housing after continued pushing force applied on the plunger causes the needle assembly to move towards a front end of the housing.

In above mentioned push type safety housing based implant/medicament injecting system, the needle assembly is engaged with the housing as the snap lock on the needle hub gets locked with the cooperative locking portion in the housing cap, produces an audible click, compresses the spring so that forward and reverse movement of the needle assembly with respect to the housing is arrested and facilitates piercing of the cannula, after removal of the protective cap, into a body, skin or tissue.

In above mentioned push type safety housing based implant/medicament injecting system, second engagement means includes a cooperative snap which resides within the housing to allow free movement of the needle assembly in a forward direction inside the housing and restrict accidental reverse motion of the needle assembly.

In above mentioned push type safety housing based implant/medicament injecting system, the seal releasing means is at the back end of the housing and includes a mating protrusion on the housing which widens the second end of the safety clip when the second end interacts with said mating protrusion and detaches the positive lock; and a releasing gap on the tongue and groove joint on which the first end of the safety clip slides; wherein said seal releasing means facilitates removal of the safety clip and enables the plunger move independently from the needle assembly so that further application of pushing force on the plunger in a forward direction in the housing independent of the needle assembly causes the plunger rod to move in the forward direction through the plunger rod guide and push the implant/medicament through the cannula into tissue.

In above mentioned push type safety housing based implant/medicament injecting system, the plunger includes a snap lock to secure the plunger within the housing after removal of the safety clip.

In above mentioned push type safety housing based implant/medicament injecting system, the first disengagement means includes a front end of the plunger and movement of the plunger towards the front end of the housing enables disengagement of the first engagement means;

the disengagement of the first engagement means is achieved by sliding said front end of the plunger over the snap lock on the needle hub to compress the snap lock on the needle hub and disengage the needle assembly from the cooperative locking portion in the housing cap; and said disengaged needle assembly automatically retracts within the housing along with the cannula by expansion of the spring.

In above mentioned push type safety housing based implant/medicament injecting system, a portion of the plunger inside said housing is retracted back with the needle assembly under due to the plunger being engaged with the needle assembly.

In above mentioned push type safety housing based implant/medicament injecting system, the second engagement means includes a locking means on the label holder to permanently couple the needle assembly in the housing after use.

BRIEF DESCRIPTION OF THE ACCOMPANYING DRAWINGS

FIG. 1a-1i illustrates a preferred embodiment of the present safety housing based implant/medicament injecting system which is a push type safety housing based implant/medicament injecting system.

FIG. 2a-2i illustrates a preferred embodiment of the present safety housing based implant/medicament injecting system which is a twist type safety housing based implant/medicament injecting system.

FIG. 3a-3h illustrates a preferred embodiment of the present safety housing based implant/medicament injecting system which is a press type safety housing based implant/medicament injecting system.

FIG. 4a-4h illustrates a preferred embodiment of the present safety housing based implant/medicament injecting system which is a hybrid type safety housing based implant/medicament injecting system.

Figure 1A:
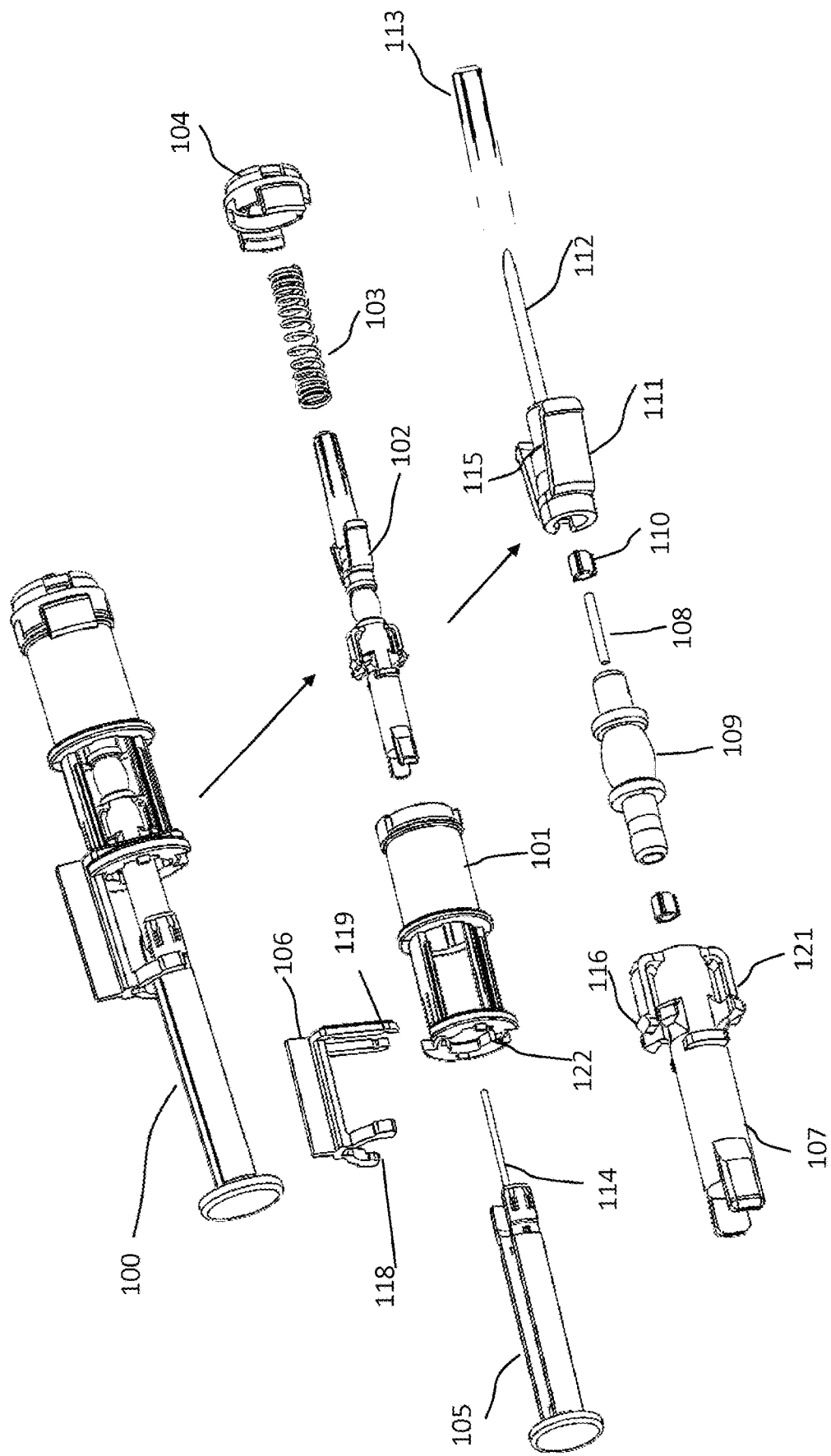

DETAILED DESCRIPTION OF THE INVENTION WITH REFERENCE TO THE ACCOMPANYING DRAWINGS

The present invention discloses a safety housing based implant/medicament injecting system for safely introducing implant/medicament or injectable substances into body/tissue of human/animal for medical or physical purposes.

The present injecting system includes a housing and an injecting syringe or needle assembly with an injecting needle/cannula. The injecting syringe or needle assembly is pre-filled with injectable substances or medicament/implant. The housing is configured to fully accommodates the needle assembly.

The housing includes a small opening at its front end. The needle assembly is fully enclosed within said housing and provided therein under support of a spring from a front end of the housing in such a manner that, the cannula, which is positioned at front end of the needle assembly, can be ejected through said front opening of the housing for piercing skin, body tissue and deliver the implant/medicament.

The injecting system also includes a plunger means. The plunger means includes a plunger rod. The plunger rod is concentrically disposed with respect to the housing, at back end of the housing and coupled with the needle assembly.

The plunger means is configured for an initial injecting plunger forward motion coupled with the needle assembly to expose the needle/cannula through the front opening of the housing and engage the needle assembly with the housing to keep the needle/cannula exposed for injection. The operative coupling between the plunger means and the needle assembly gets released at the end of the initial injecting plunger forward motion. This enables the plunger means for a subsequent continuing injecting plunger forward motion. The plunger rod enter in the needle assembly during the subsequent continuing injecting plunger forward motion to inject the implant/medicament through the exposed needle/cannula.

In the present injecting system, the plunger means is coupled with the needle assembly by a releasable seal means during the initial injecting plunger forward motion. This coupling ensures transferring of a pushing force applied on the plunger means to the needle assembly and co-forward movement of the plunger means and the needle assembly inside the housing by compressing the spring until a first engagement means engages the needle assembly with the front end of the housing. In this engaged condition, the cannula is completely ejected through the front opening and any forward or backward motion of the needle assembly is arrested.

The plunger means, for its subsequent continuing injecting plunger forward motion, is decoupled from the needle assembly by a seal releasing means. The seal releasing means is configured to open the releasable seal means to decouple the plunger means from the needle assembly. The decoupling of the plunger means from the needle assembly enables independent forward movement of the plunger means inside the housing upon continuing application of the pushing force on the plunger means. This independent forward movement of the plunger means causes forward movement of the plunger rod in the needle assembly for pushing the implant/medicament through the cannula into the tissue.

The present safety housing based implant/medicament injecting system also includes a first disengagement means. The first disengagement means is configured to disengage the first engagement means upon completing delivery of the implant/medicament and thereby enable the automatic retraction of the needle assembly with the cannula in the housing under bias of the spring. The retracted needle assembly is locked within the housing with the help of a second engagement means. This avoids any future use/accidental exposure of the used needle/cannula.

In a preferred embodiment of the present safety housing based implant/medicament injecting system, the injecting needle/cannula may be covered with a removable protective cap. The inner surface of the housing and outer surface of the needle assembly includes cooperative guiding means to arrest any unwanted rotation of the needle assembly within the housing. Also, the needle assembly may includes forward snap which sits within the housing and configured to freely move in the forward direction inside the housing to prevent any accidental reverse movement of the needle assembly.

Figure 1B:
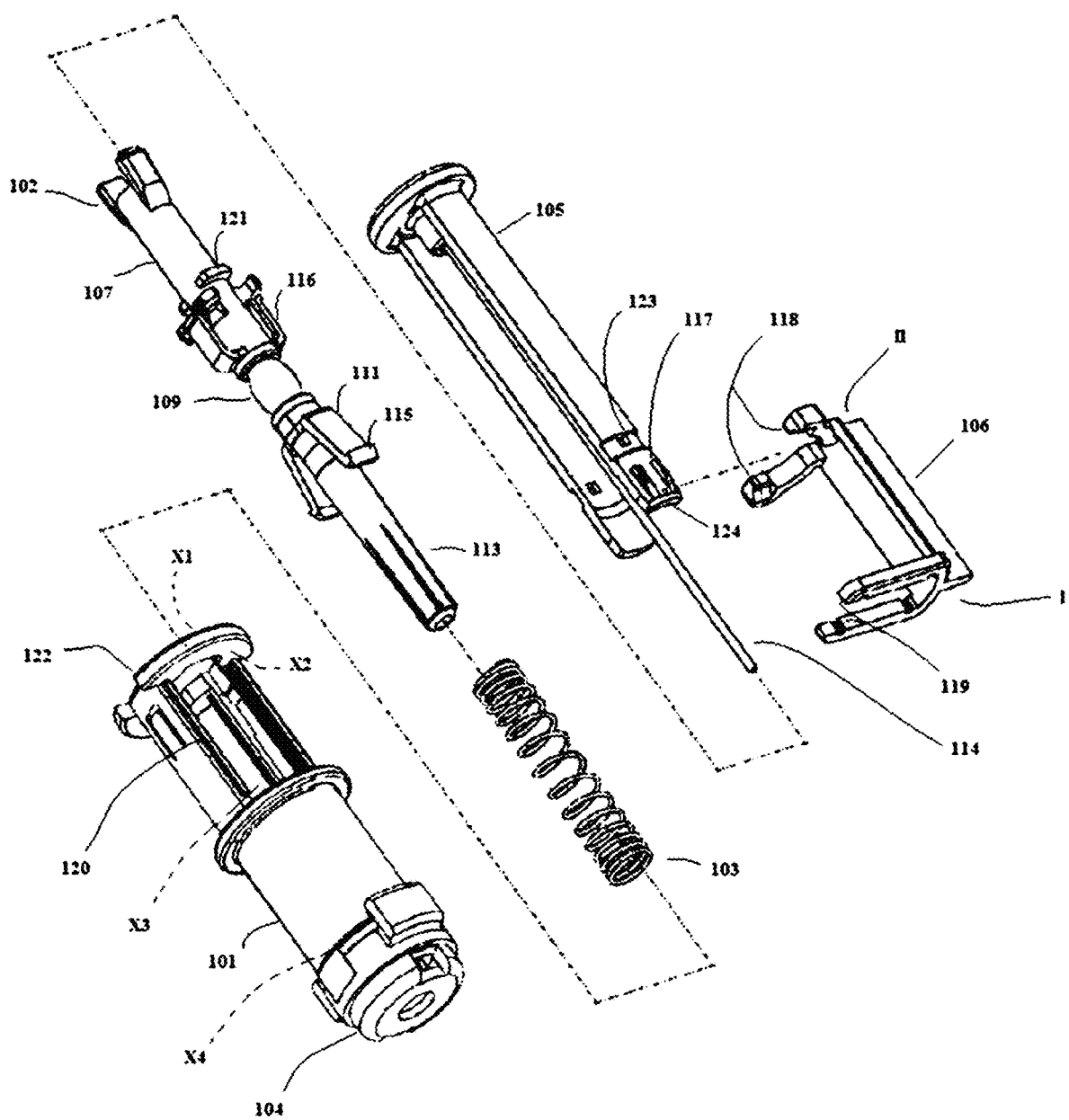

Reference is first invited from the accompanying FIGS. 1a and 1b which shows the present injecting system embodiment with push type safety housing. As shown in the referred figures, the push based pre-filled medicament injecting device 100 includes a needle assembly 102. The needle assembly 102 is fully enclosed within a housing 101. The housing 100 is preferably a cylindrical barrel. The needle assembly 102 is secured within the housing 101 and supported by a spring 103 with respect to housing front top or cap 104.

A back end of the needle assembly 102 is coupled with a plunger 105 by a safety clip 106.

The needle assembly 102 includes a label holder 107 at the back end of the needle assembly 102. A plunger rod guide 110 which runs through implant magnifier cum container 109 is positioned between the label holder 107 and a needle hub 111. The plunger rod 114 can moves through the plunger rod guide 110 to pushes implant or the injectable substances 108 in the implant container 109 towards the needle hub 111. The needle hub 111 houses a cannula 112. The cannula 112 has a fluid communicable connection with the plunger rod guide 110 to receive the implant or the injectable substances 108. The cannula 112 is adapted to eject through the small opening 104a defined in the housing top 104 and penetrates the body or tissue to delivers the implant or the injectable substances 108. A protective cap 113 is provided on the cannula 112.

The needle hub 111 is coupled with inner surface of the housing 101 by a tongue and groove joint. This coupling arrests any rotational movement of the needle assembly 102 in the housing 101. However, the tongue and groove joint allows spring biased forward and backward motion of the needle assembly 102 within the housing 101. The needle hub 111 includes a snap lock 115. The snap lock 115 is configured to engage with cooperative locking portion in the housing front top or cap 104. The snap lock 115 and cooperative locking portion in the housing top 104 constitutes the first engagement means of the present embodiment.

The label holder 107 includes a snap 116. The snap 116 is configured to sits within the barrel 101 and freely move only in the forward direction. This restricts the accidental reverse motion of the needle assembly 102.

The first end (I) of the safety clip 106 is coupled with the housing 101 and the needle assembly 102. The second end (II) of the safety clip 106 is coupled with the plunger 105 by a positive lock. This whole arrangement constitutes the releasable seal means of the present embodiment.

Figure 1C:
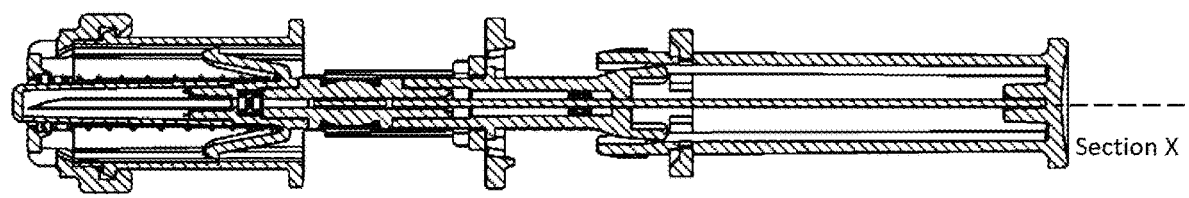
Figure 1C:
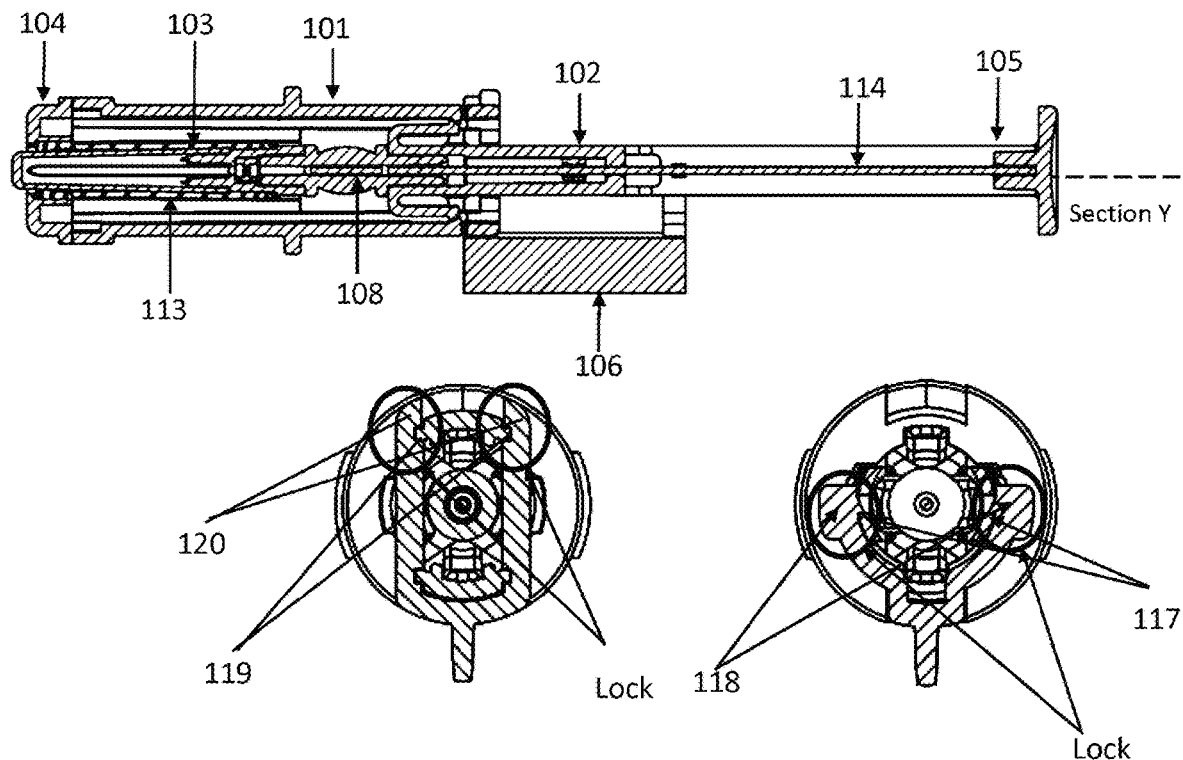
Figure 1C:
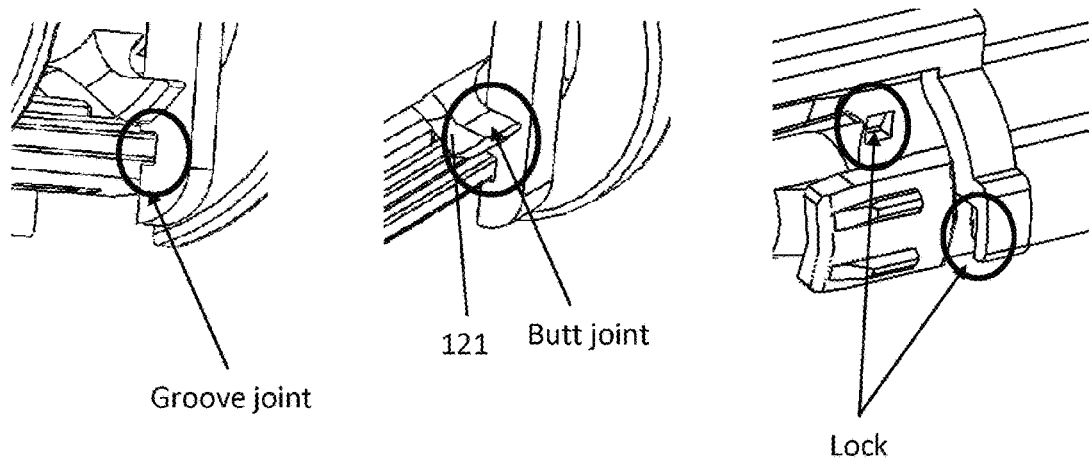

Reference is next invited from the accompanying FIG. 1c, which shows a cross sectional view of the present injecting system.

As shown in the accompanying FIGS. 1a, 1b and 1c, at least one external opening or slot 117 is provided in the plunger 105. A cooperative protrusion 118 is provided on the second end (II) of safety clip 106. This protrusion 118 is configured to be detachably engaged with said opening or slot 117.

The first end (I) of the safety clip 106 includes tongue 119 and groove 120 joint. The first end (I) of the Safety clip 106 also includes butt 121 which is coupled with the label holder 107 of the needle assembly 102. The tongue and groove (119, 120) joint based coupling between the housing 101 and the safety clip 106 enables the safety clip 106 to slides through the housing 101. A pushing force applied on the plunger 105 is transferred to the needle assembly 102 via the safety clip 106. This enables co-movement of the plunger 105 and the needle assembly 102.

The safety clip 106 ensures that, the plunger 105 does not become loose part.

In the initial stage, as shown in the FIG. 1c, the needle assembly 102 and the cannula 112 covered with protective cap 113 is held within the housing 101 by bias of the spring 103. When the pushing force is applied on the plunger 105, the force is transferred to the needle assembly 102 through the safety clip 106. This drives both the plunger 105 and the needle assembly 102 in a forward direction within the housing 101. In this stage, the plunger rod 114 cannot move through the plunger rod guide 110 as the plunger rod 114 also moves with the plunger 105 and the needle assembly 102.

Figure 1D:
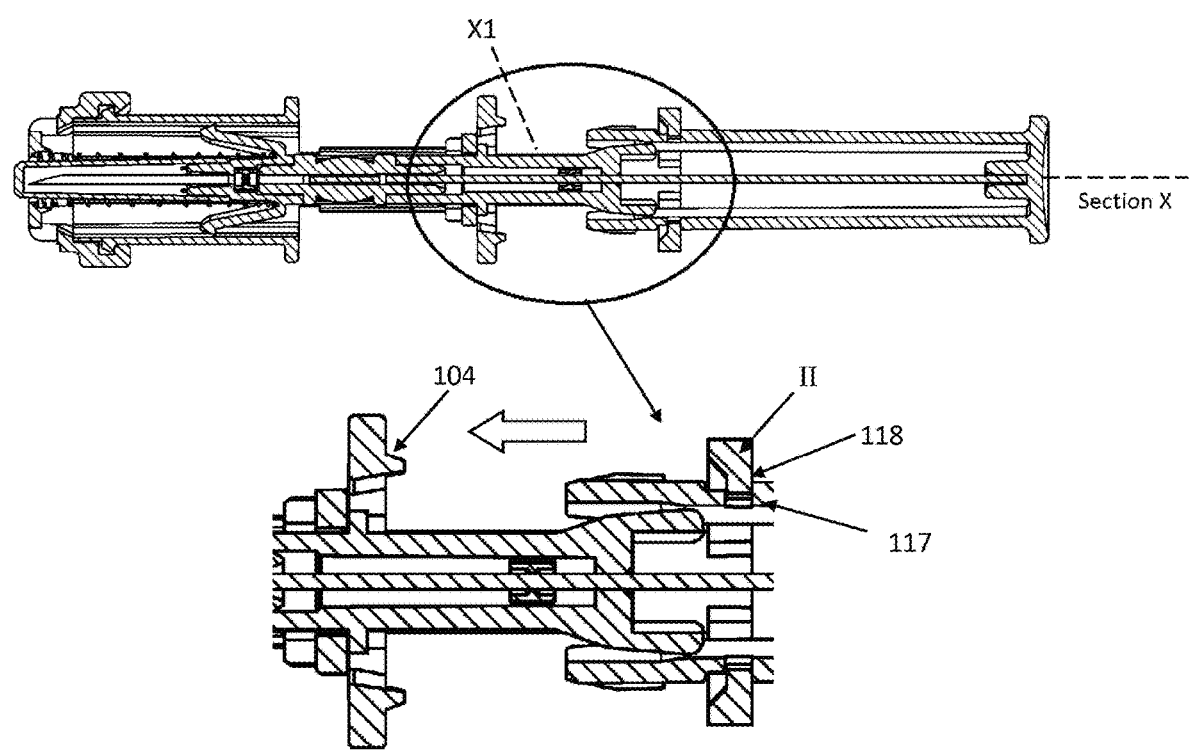

On continued application of the pushing force on the plunger 105, the cannula 112 covered with protective cap 113 is completely ejected the housing 101. In this stage, the second end (II) of the safety clip 106 slides within mating protrusion 122 of the housing 101. This widens the second end (II) of the safety clip 106 and disengages the positive lock as the protrusion 118 comes out of from the slot 117. This shown in the accompanying FIG. 1d. The first end (I) of safety clip 106 slides within the tongue 120 of the housing 101 and gets released at point X3. Ends of the tongue 120 facilitate removal of safety clip 106. The above arrangement constitutes the seal releasing means of the present embodiment.

A snap lock 123 of the plunger 105 also gets locked within the housing 101 at point X2. The situation is shown in the accompanying FIG. 1e.

At this stage, the spring 103 is fully compressed, as the snap lock 115 of the needle hub 111 is engaged with cooperative locking portion in the housing top 104 with an audible click sound, as shown in the FIG. 1e. This ensures that the forward and reverse movement of the needle assembly 102 is being arrested.

The safety clip 106 is now free to be pulled out of the assembly. After, the needle assembly 102 gets locked into the housing 101, the protective cap 113 can be removed as shown in the accompanying FIG. 1f. The needle cannula 112 then can pierce body/tissue.

The removal of the safety clip 106, disengages the plunger 101 from the needle assembly 102 and thereafter further application of the force on the plunger 105, moves the plunger rod 114 starts to move in forward direction through the rod guide 110 and push the implant 108 through the cannula 112, into the tissue, as shown in the accompanying FIG. 1g.

At the end of the injection stage, outer body plunger 105 slides over the snap lock of the needle hub 111 and at the last point of the plunger movement towards distal end, the plunger front end 124 compress the snap lock 115 to disengaged from the housing top 104, as shown in the FIG. 1h. Herein, the plunger front end 124, acts as the first disengagement means of the present embodiment.

When the snap lock 115 is disengaged, the needle assembly 102 moves in backward direction with expansion of the spring 103. This results retraction of the cannula 112 from the skin along with the plunger 105. The needle assembly 102 with the cannula 112 then gets secured inside the housing 101. During the needle retraction from the skin, the plunger is also retracted back as it has an engagement with the needle assembly at point X4.

At the end of the retraction stage, label holder 107 gets snap locked with the housing at Point X2, as shown in the accompanying FIG. 1i. This constitutes the second engagement means of the present embodiment. After retraction stage, the needle assembly 102 is permanently arrested inside the housing 101, thus rendering the needle assembly useless & can only be disposed off.

In this stage, the plunger will not be able to push the needle assembly in forward direction as it is locked at point X2 within the housing. The Plunger has a freedom to move only backward which anyway is harmless to user/Patient.

Figure 2B:
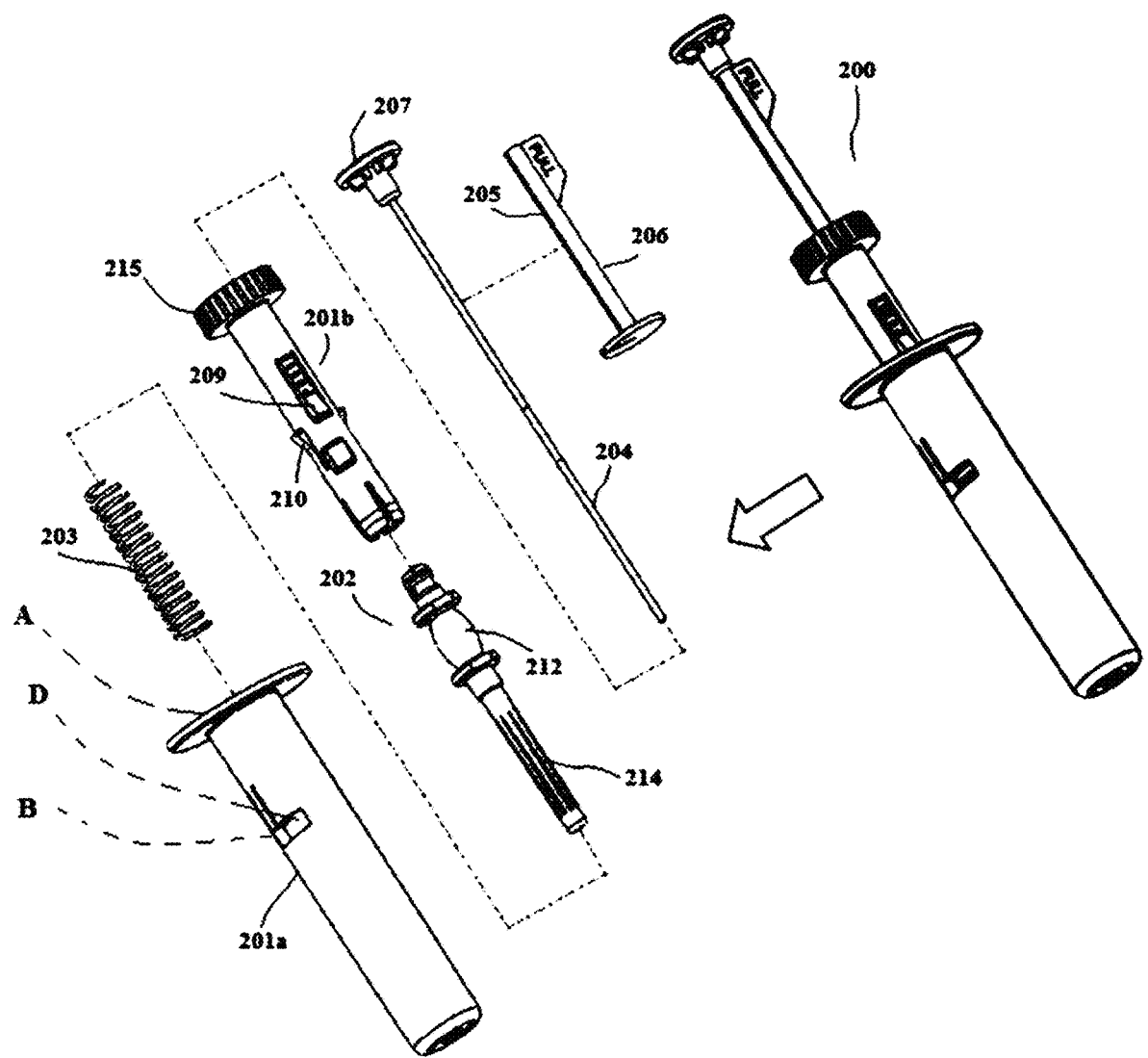

Reference is next invited from the accompanying FIGS. 2a and 2b which shows a preferred embodiment of the present injecting system with twist based operable safety housing. As shown in the referred figures, the twist based prefilled medicament injecting device 200 includes a needle assembly 202 and an enclosing means. The enclosing means is divided in two parts viz. an outer housing 201a and an inner housing 201b, wherein, the outer housing 201a is configured to fully enclose the needle assembly 202 and the inner housing 201b is coupled to distal end of the outer housing 201a and configured to telescopically move within the outer housing 201a.

The needle assembly 202 is supported by a spring 203 within the outer housing 201a. Back end of the needle assembly 202 is coupled to a plunger rod 204 by a supportive safety cap 206. Back end of the plunger rod 204 includes a plunger cap 207. The coupling point between the plunger rod 204 and the back end of the needle assembly 202 is surrounded by the inner housing 201b.

One end of the safety cap 206 is locked inside the inner housing 201b, and other end of the safety cap is coupled with the with plunger cap 207 by a butt joint. The safety cap 207 has a slot or opening 205 running through its length to ensure its engagement with the plunger rod 204.

The locking of the safety cap 206 with the inner housing 201b by the butt joint, as shown in the accompanying FIG. 2c, ensures that the plunger rod 204 does not become loose part. The Butt joint between the safety cap 206 and the plunger cap 207 ensures that the plunger rod 204 does not move independently with respect to inner housing 201b. It also ensures that the force applied on the plunger cap 207 gets transferred to the inner housing 201b and the needle assembly 202 via the safety cap 206 during needle ejection stage.

The inner housing 201b has a forward snap 209 on its external surface which is locked at Point A to ensure that the needle assembly 202 does not move forward. The inner housing 201b also includes a reverse snap 210, which sits inside groove of the outer housing 201a and freely move in forward direction. The reverse snap 210 and the groove of the outer housing 201a ensure that the inner housing 201b does not rotate during the needle ejection stage.

The outer housing 201a has a forward snap 211 which holds the needle assembly against the spring at Point B to ensure that the needle assembly 202 does not become loose part.

The needle assembly 202 includes a needle holder 212 and a cannula 213 having a fluid communicable connection with the needle holder 212. The plunger rod 204 can move through the needle holder and push implant or the injectable substances 208, which are prefilled within the needle holder 212, in forward direction to supply the implant or the injectable substances in the cannula. The cannula is adapted to eject through a small opening in the outer housing 201a and penetrate within the body or tissue and deliver the implant or the injectable substances. A protective cap 214 is provided on the cannula 213.

In the initial stage as shown in the FIG. 2c, the needle assembly 202 with the protective cap 214 covering the cannula 213 is held within the outer housing 201a under tension of the spring 203. To eject the needle out of the outer housing 201a, the lock at Point A is released by pressing the forward snap 209 down. After releasing the lock at Point A, applied force on the plunger cap 207 is transferred to the needle assembly 202 through the safety cap 206 which drives the needle assembly 202 surrounded with the inner housing 201b in forward direction through the outer housing 201a with the plunger rod 204. During this driving of the needle assembly 202, the implant 208 does not move independently with respect to the needle assembly 202 as the plunger rod 204 cannot move through the needle holder 212 due to the safety cap 206 supported cooperative movement of the plunger rod 204 and the needle assembly 202. In this embodiment the safety cap acts as the releasable seal means.

Figure 2E:
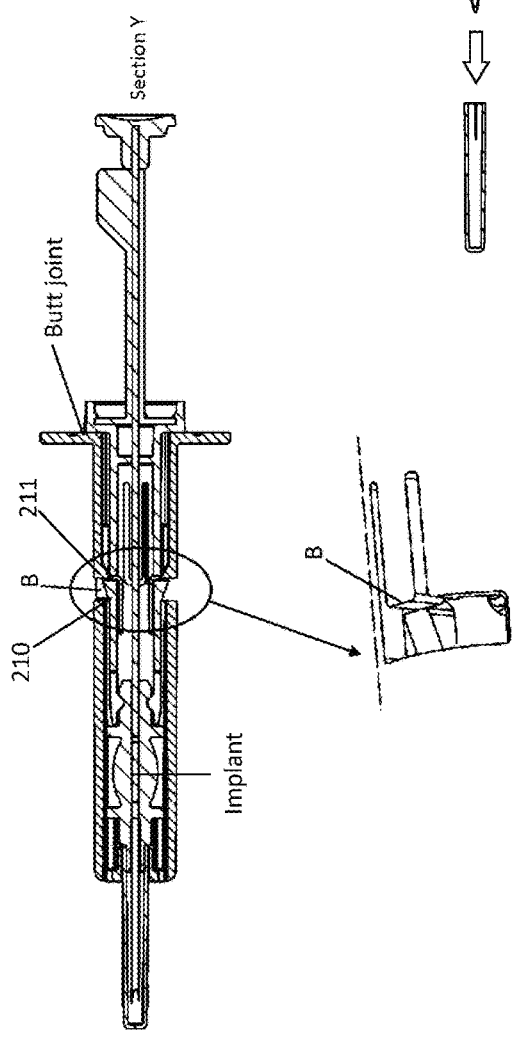

On application of force on the plunger cap 207, the cannula 213 is completely ejected out along with the protective cap 214 from the outer housing 201a. In this stage, as shown in the FIGS. 2d and 2e, the reverse snap 210 of the inner housing 201b is moved forward within the tongue and grove joint and gets locked with the forward snap lock 211 in the outer housing 201a at Point B with an audible click sound. The spring 203 gets fully compressed in this stage and the needle assembly 202 gets engaged with the outer housing 201a at Point B to ensure that the reverse movement of needle assembly 202 is arrested. Forward movement of the needle assembly 202 is arrested by having a butt joint between the inner and the outer housing. The combination of the reverse snap 210 and the forward snap lock 211 acts as first engagement means. The stressed forward snap 209 of the inner housing at Point C rides within the inner surface of the outer housing (FIG. 2d).

Figure 2F:
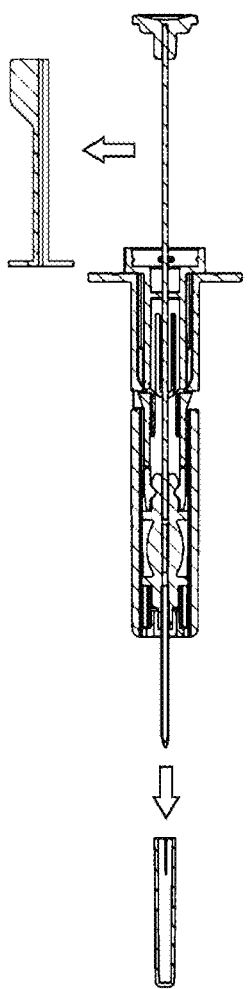

The safety cap 206 can be pulled out from the assembly, which makes the plunger rod 204 moveably independent of the needle assembly 202. The safety cap 206 thus can performs as the seal releasing means. The protective cap 214 can be removed, as shown in the accompanying FIG. 2f, for exposing the cannula 213 and piercing into the body/tissue by only holding the housing.

Figure 2G:
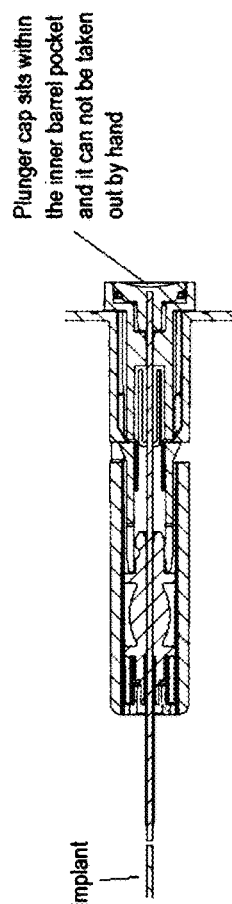

Now, further application of the force on the plunger cap 207, enables the plunger rod 204, which is now independent of the needle assembly 202 due to removal of the safety cap 206, to moves in forward direction and push the implant 208 through the cannula 213, into the tissue, as shown in the accompanying FIG. 2g. At the end of the injection stage, the plunger cap 207 sits within the inner housing pocket and it cannot be taken out by hand.

At the end of the injection stage, to retract the cannula from the skin, the inner housing needs to be rotated by holding the grip area 215 in counter clockwise direction. The present embodiment includes a circular snap between the needle assembly and the outer housing to acts as the first disengagement means for disengagement of the engaged disposition between the needle assembly and the outer housing.

Figure 2H:
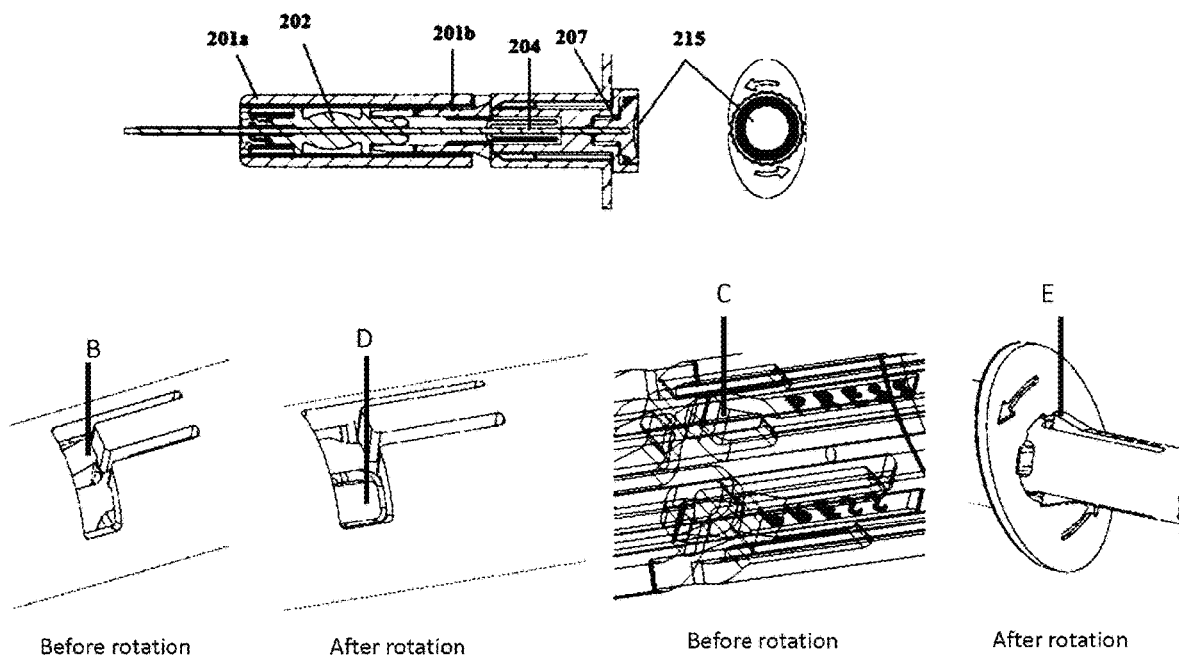

In this stage, as shown in the accompanying FIG. 2h, the inner housing 201b and the plunger rod 204 & cap 207 will rotate and the needle assembly 202 will not rotate due to rotation arresting circular snap between the needle assembly 202 and the outer housing 201a. The integrated Rotation of inner housing 201b, the plunger rod and the plunger cap with respect to the outer housing 201a disengages the lock of the reverse snap 210 with the outer housing 201a at Point B & reaches to the Point D at outer housing 201a. The stressed forward snap 209 of the inner housing at Point C which rides within the inner surface of the outer housing stays at Point E.

Figure 2I:
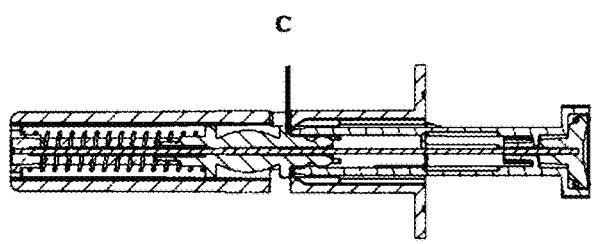

When the lock of inner housing 201b is disengaged from the outer housing 201a, the compressed spring 203 gets expanded which moves the needle assembly in backward document and retract the cannula 213 from the skin automatically along with the plunger & gets secured inside the outer housing. At the end of the retraction stage, the second engagement means which includes a lock between the needle holder and the forward snap lock permanently arrests the needle assembly in the outer housing at point C as shown in FIG. 2i, thus rendering the syringe use less & can only be disposed off. The plunger will not push the needle assembly forward, as it is locked at point E on the outer housing.

Reference is next invited from the accompanying FIGS. 3a and 3b which show a preferred embodiment of the present injecting system with press based operable safety housing. As shown in the referred figures, injecting system 300 includes a needle assembly 302 which is fully enclosed within a housing 301 preferably a cylindrical barrel. The needle assembly 302 is secured within the housing 301 support of a spring 303 positioned between housing top 304 and front end of the needle assembly 302. Back end of the needle assembly 302 is coupled with a plunger 305 with an insert molded rod 314. A press button 306 is provided on the housing 301 at a selected position between the proximal and distal end of the housing 301.

The needle assembly 302 includes a label holder 307 at its back end, a plunger rod guide 310 running through an implant container cum magnifier 309 and positioned in an axially symmetric manner between the label holder 307 and a needle hub 311. The plunger rod 314 can move through the plunger rod guide 310 and push implant/medicament or the injectable substances 308 which are prefilled within the plunger rod guide 310 towards the needle hub 311. The needle hub 311 houses a cannula 312 having fluid communicable connection with the plunger rod guide 310 to receive the implant or the injectable substances 308. The cannula 312 is adapted to penetrate within the body or tissue and deliver the implant or the injectable substances 308. A protective cap 313 is provided on the cannula 312.

The needle hub 311 includes snap lock 315 which is configured to engage with cooperative locking portion in the housing top 304 and act as the first engagement means. The label holder 307 includes a snap lock 316 which sits within the housing 301 and free to move in the forward direction, inside the housing 301.

Back end of the label holder 307 includes across flat surface 317 which is configured to engage with inner surface of the housing 301 to arrest any rotational movement of the needle assembly 302 with respect to the housing 301 and allow only spring biased forward and backward motion of the needle assembly 302 within the housing 301.

Figure 3C:
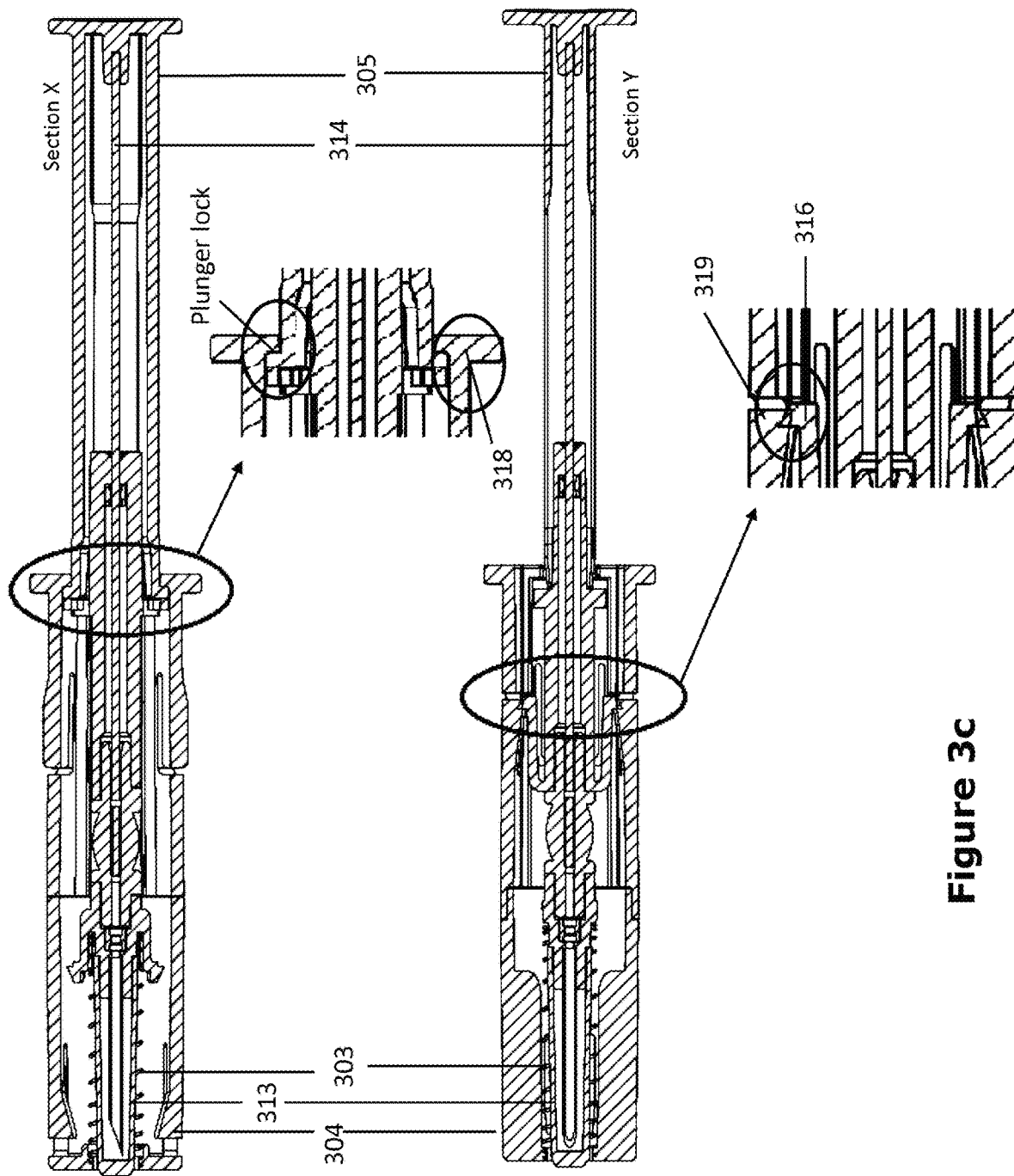

Reference is next invited from the accompanying FIG. 3c which shows cross sectional views of the present injecting system with press based operable safety housing along with engagement mechanism between the housing 301, the needle assembly 302 and the plunger 305.

As shown in the accompanying FIGS. 3a, 3b, 3c, the plunger 305 is irremovably secured inside the housing 301 and the plunger outer body is coupled with the with the label holder 318 of the needle assembly 302 by using a butt joint 318 which ensures that the pushing force applied on the plunger 305 gets transferred to the needle assembly 302 via the butt joint 318 and causing cooperative movement of the needle assembly 302 and the plunger 305. The butt joint acts as the releasable seal means.

In the initial stage, the needle assembly 302 with the protective cap 313 covering the cannula 312 is held within the housing 301 under tension of the spring 303. The snap lock 316 of the label holder 307 is held just above its cooperative mating snap portion 319 in the housing 301.

When a Force is applied on the plunger 305, the force is transferred to the needle assembly 302 through the butt joint 318 in the label holder of the needle assembly 302 which drives the needle assembly 302 inside the housing 301 in forward direction. During this driving of the needle assembly 302, the implant 308 does not move independently with respect to the needle assembly 302 as the plunger rod 314 cannot move through the plunger rod guide 310 due to the butt joint 318 supported cooperative movement of the plunger 305 and the needle assembly 302.

With the continued application of force on the plunger 305, the cannula 312 is completely ejected out along with the protective cap 313 from the housing 301. During this stage, the spring 303 gets fully compressed and the needle assembly gets engaged with the housing at point A, as the snap lock 315 of the needle hub 311 is engaged with cooperative locking portion in the housing top 304 with an audible click sound, as shown in the FIG. 3d. This ensures that the forward and reverse movement of the needle assembly 302 is arrested. The front end 319 of plunger outer body which is coupled with the needle assembly 302 at the butt joint 318 reaches the region of Press button 306 on the housing 301 at point 'B'. The press button act as the seal releasing means.

After, the needle assembly 302 gets engaged with the housing top 304 with the cannula 312 is completely ejected out along with the protective cap 313 from the housing 301, the protective cap 313 is removed as shown in the accompanying FIG. 3e. The needle cannula 312, after removal of the cap, can be pierced into the body/tissue by only holding the housing. Now, application of a gentle force on the press button 306 on the housing 301 disengages the butt joint 318 based engaged disposition between the needle assembly and the plunger 305.

Now further application of force on the plunger 305, the plunger body, which is now independent of the needle assembly due to disengagement of the Butt joint 318 between needle assembly and the plunger front end, moves in forward direction and push the rod 314 through the rod guide 310 and deliver the implant/medicament 308 through the cannula 312, into the tissue as shown in the accompanying FIG. 3f.

At the end of the injection stage, plunger outer body slides over the snap locking feature of the needle hub 311 at point A and at the last point of the plunger movement towards distal end, the plunger front end forces the snap lock 315 of the needle hub 311 to compress and disengage from the lock of the housing top 304 at the point A. Herein the plunger front end act as the first disengagement means.

When the snap lock 315 of needle assembly is disengaged from the housing 301, the compressed spring 303 gets expanded which moves the needle assembly 302 in backward direction to retract the cannula 312 from the skin automatically along with the plunger 305. During the needle retraction from the skin, the plunger 305 is also retracted back as the plunger portion inside the housing has an engagement with the needle assembly 302.

At the end of the retraction stage, the label holder 307 in the needle assembly gets snap locked with the housing at Point C as shown in the accompanying FIG. 3h. In this retraction stage, the needle assembly 302 is permanently arrested inside the housing, thus rendering the syringe use less & can only be disposed off. The Plunger 305 has a freedom to move only backward which anyway is harmless to user/Patient. Herein, the snap lock 316 on the label holder act as the second engagement means.

Figure 4A:
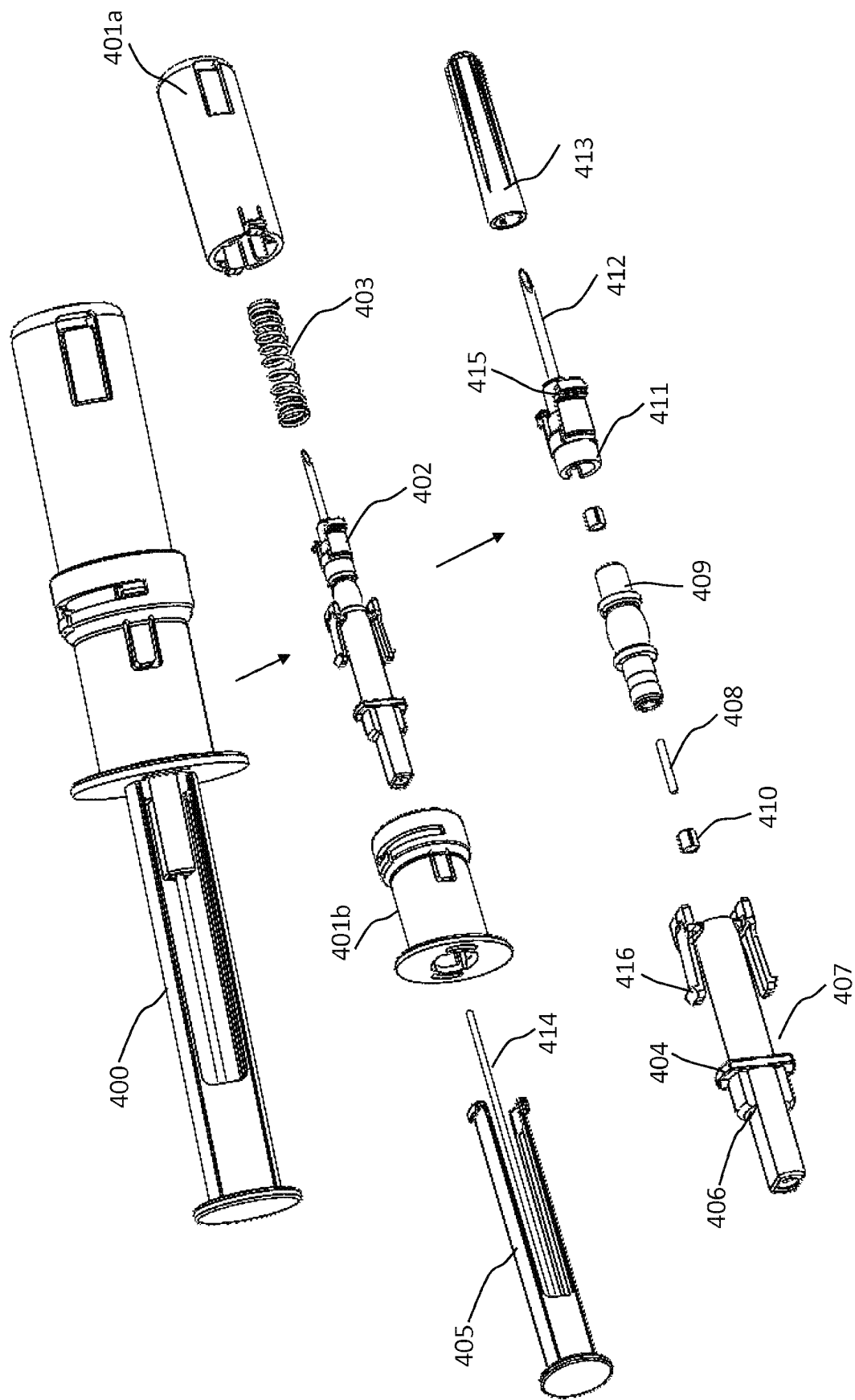
Figure 4B:
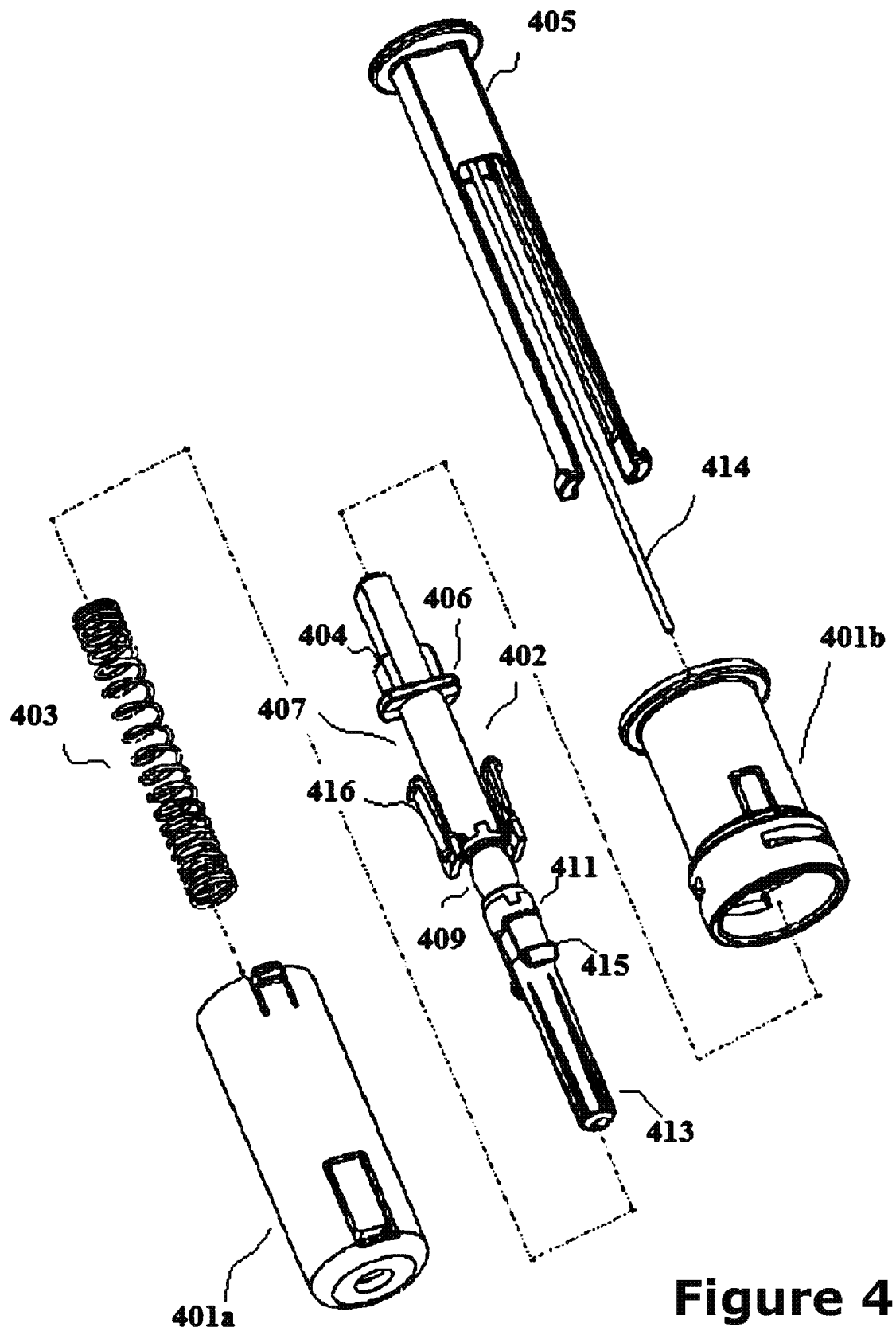

Reference is next invited from the accompanying FIGS. 4a and 4b which are showing a preferred embodiment of the present prefilled medicament injecting device with hybrid safety housing. As shown in the referred figures the hybrid prefilled medicament injecting device 400 includes a needle assembly 402 which is fully enclosed within a housing. The housing is comprising of a top housing 401a and a bottom housing 401b. The top bottom housings 401a & 401b are axially coupled to each other.

The needle assembly 402 is secured within the housing 401a & 401b and supported by spring 403. The spring is positioned between the top housing 401a and front end of the needle assembly 402. Back end of the needle assembly 402 is coupled with a plunger 405. The plunger 405 includes an insert molded rod 414.

The needle assembly 402 includes a label holder 407 at its back end, a needle hub 411 at its front end, and a plunger rod guide 410. The plunger rod guide 410 is running through an implant container cum container 409 and positioned between the label holder 407 and the needle hub 411 in an axially symmetric manner. The plunger rod 414 is configured to move through the plunger rod guide 410 and push implant/medicament or the injectable substances 408 in the plunger rod guide 410 towards the needle hub 411. The needle hub 411 houses a cannula 412 which has a fluid communicable connection with the plunger rod guide 410 to receive the implant or the injectable substances 408. The cannula 412 is adapted to penetrate within the body or tissue and deliver the implant or the injectable substances 408. A protective cap 413 is provided on the cannula 412.

The needle hub 411 includes a snap lock 415 which acts as the first engagement means. The snap lock 415 is configured to engage with cooperative top locking portion in the top housing 401a. The label holder 407 includes a snap lock 416, which can sits within the housings 401a and 401b and free to move in the forward direction.

Back end of the label holder 407 includes a lateral flat surface 406. The lateral flat surface 406 is configured to selectively engage with inner surface of the housings to selectively arrest any rotational movement of the needle assembly 402 with respect to the housings. The lateral flat surface 406 allow only spring biased forward and backward motion of the needle assembly 402 within the housings.

Figure 4C:
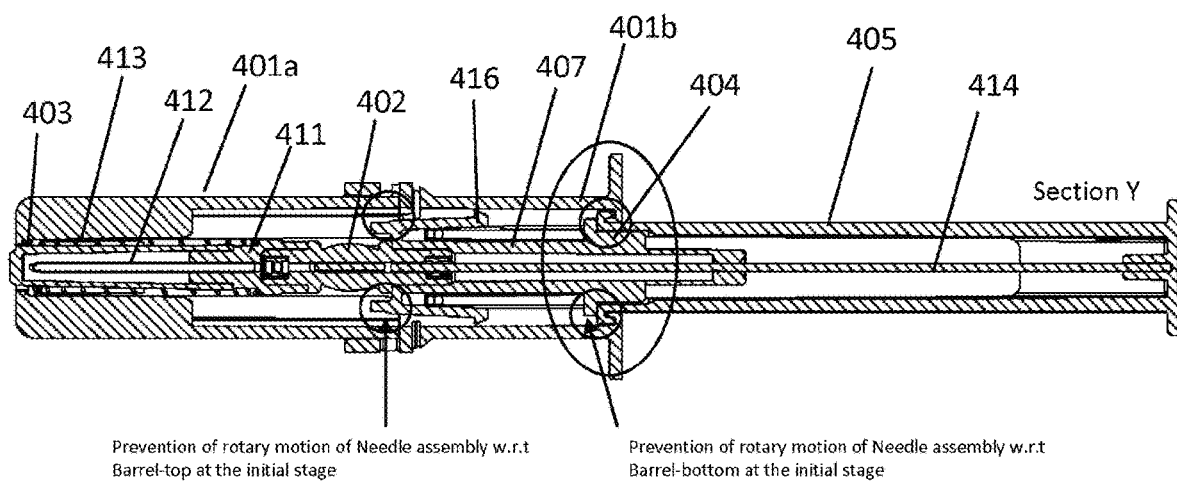
Figure 4D:
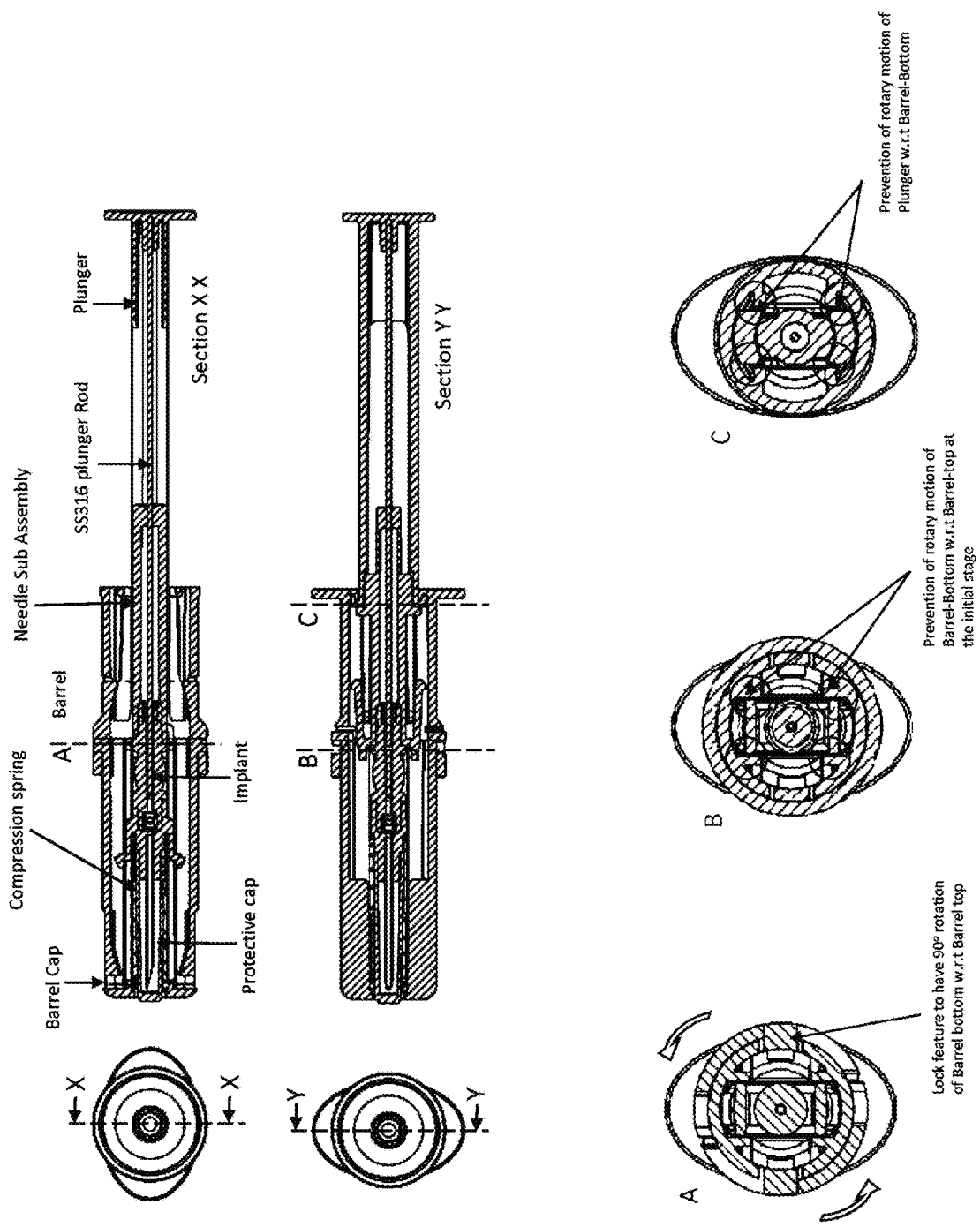

Reference is next invited from the accompanying FIGS. 4c and 4d which are showing cross-sectional view of the present prefilled medicament injecting device with engagement mechanism between the housings, the needle assembly 402 and the plunger 405.

As shown in the accompanying FIGS. 4a, 4b, 4c, 4d, the plunger 405 is ir-removably secured inside the bottom housing 401b and the plunger outer body is coupled with the with the needle assembly 402 by a butt joint 404 on the label holder 407. This coupling acts as the releasable seal means and ensures that the pushing force applied on the plunger 405 gets transferred to the needle assembly 402 via the butt joint 404. This causes cooperative movement of the needle assembly 402 and the plunger 405.

At the initial stage, front portion of the needle assembly 402 is enclosed by the top housing 401a and back portion of the needle assembly 402 is enclosed by the bottom housing 401b. In this stage, rotation of the needle assembly 402 with respect to the top housing 401a and the bottom housing 401b is arrested by the locking surface. More specifically, in his stage, rotational movement of the bottom housing 401b w.r.t. the top housing 401a is arrested by lateral flat surface 406 engagement of the needle assembly 402 with inner surface of the top housing 401a and lateral flat surface 406 engagement of the needle assembly 402 with inner surface of the bottom housing 401b. The rotational movement of the plunger w.r.t the bottom housing 401b is arrested by lateral flat surface engagement of the Plunger with the bottom housing.

When a Force is applied on the plunger 405, the force is transferred to the needle assembly 402 through the butt joint 404. This drives the needle assembly 402 inside the housing in forward direction. During this forward motion of the needle assembly 402, the implant 408 does not move, as the plunger rod 414 cannot move through the plunger rod guide 410 due to the butt joint 404 supported cooperative movement of the plunger 405 and the needle assembly 402.

Continuing application of the force on the plunger 405, enables the cannula 412 to completely ejected out along with the protective cap 413 from the housing. During this stage, as shown in the FIG. 4e the spring 403 gets fully compressed and the needle assembly is engaged with front of the top housing 401a at point A, as the snap lock 415 of the needle hub 411 is engaged with cooperative locking portion in the front of the top housing 401a with an audible click sound. This engagement arrests the forward and reverse movements of the needle assembly 402. Front end of plunger outer body, which is coupled with the needle assembly 402 at the butt joint 404, reaches at point 'B', where joining surface between the top and the bottom housings lies with lateral flat surface releasing gap in housing inner surfaces. This lateral flat surface releasing gap acts as the seal resealing means (FIG. 4e).

In the lateral flat surface releasing gap, the surface engagement between needle assembly 404 and the bottom housing 401b is released, permitting rotation of the top housing 401a and the needle assembly 402 w.r.t the bottom housing 401b.

Now, holding the top housing 401a, a rotation of the bottom housing 401b in 90° clockwise direction will disengage the butt joint 404 between the plunger 405 and needle assembly 404 with an audible click sound. During this rotation, the needle assembly 402 which is coupled to the top housing 401a does not rotate, but the bottom housing and the plunger 405 rotates 90° w.r.t the needle assembly 402, due to the lateral flat engagement of plunger with the bottom housing 401a. A lock feature is provided in the bottom housing 401b to restricts rotation in CCW direction once it is rotated in CW direction.

After, the needle assembly 402 is engaged with the top housing 401a, and the cannula 412 is completely ejected out along with the protective cap 413 from the housing, the protective cap 413 is removed, as shown in the accompanying FIG. 4f.

The needle cannula 412, after removal of the cap, is pierced into the body/tissue by only holding the housing. In this stage, further application of the force on the plunger 405, the plunger body, which is disengaged from the needle assembly 402, moves in forward direction and push the rod 414 through the rod guide 410 to deliver the implant 408 through the cannula 412, into the tissue, as shown in the accompanying FIG. 4g.

At the end of the injection stage, plunger outer body slides over the snap locking feature of the needle hub 411 (at point A) and the plunger front end forces the snap lock 415 to compress and disengage from the lock with the front of the top housing top. Herein, the plunger outer body act as the first disengagement means.

When the snap lock 415 of needle assembly is being disengaged from the housing 401, the compressed spring 403 gets expanded and moves the needle assembly 402 in backward direction to retract the cannula 412 from the skin automatically along with the plunger 405. During the needle retraction from the skin, the plunger 405 is also retracted back, as the plunger portion inside the housing has an engagement with the needle assembly 402.

Figure 4H:
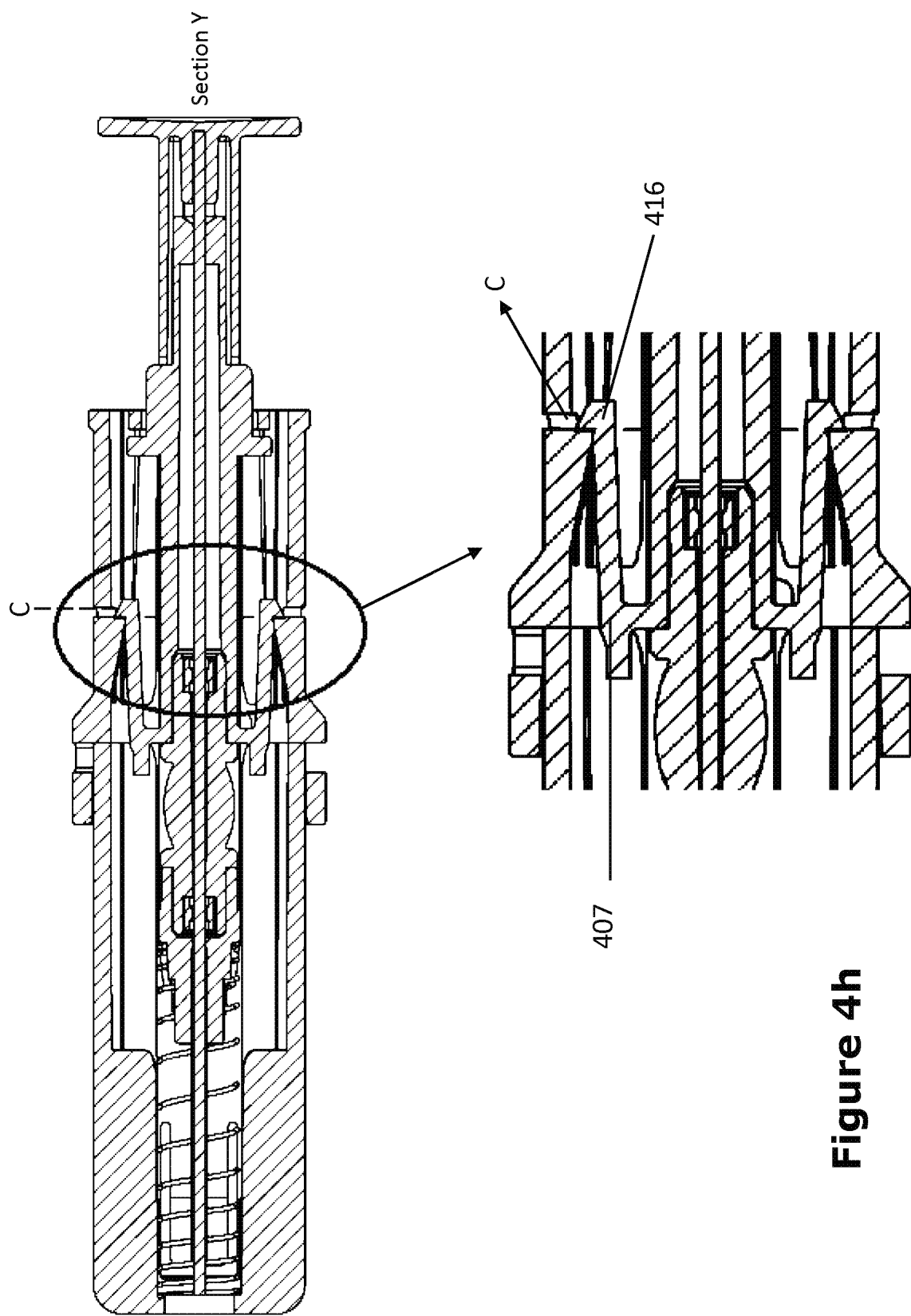

At the end of the retraction stage, the label holder 407 in the needle assembly gets snap locked with the housing (at Point C as shown in the accompanying FIG. 4h). Herein, the snap lock of the label holder 407 acts as the second engagement means. In this stage, the Needle assembly 402 is permanently arrested inside the housing, thus rendering the syringe use less.

The invention claimed is:

1. A safety housing based implant/medicament injecting system comprising:
   a housing comprising a cylindrical barrel with a housing cap at a front end of the cylindrical barrel and an opening defined in the housing cap;
   a needle assembly fully accommodated within the housing and supported by a spring positioned between the housing cap and a front end of the needle assembly, said needle assembly includes
   a needle hub comprising a cannula at the front end of the needle assembly;
   a label holder at a back end of the needle assembly;
   an implant/medicament container positioned in an axially symmetric manner between the label holder and the needle hub; and
   a plunger rod guide running through the implant/medicament container;
   a plunger means comprising a plunger and a plunger rod, said plunger means is configured for:
   an initial forward motion of the plunger to eject the cannula through the opening, wherein a safety clip at a back end of the housing operatively couples the plunger and the plunger rod with the label holder of the needle assembly and a first engagement means engages the needle hub with the housing at an end of the initial forward motion of the plunger; and
   a subsequent continuing forward motion to inject the implant/medicament through the ejected cannula when a seal releasing means operates on the safety clip for removal of the safety clip which disengages the label holder from the plunger, wherein the plunger rod guide enabling the plunger rod to move through said plunger rod guide and push the implant/medicament towards the needle hub;
   a first disengagement means for disengaging the first engagement means; and
   a second engaging means to permanently arrest the needle assembly in the housing after use;
   wherein the safety clip comprising a first end coupled with both the housing and the label holder and a second end externally coupled with the plunger by using a positive lock.

2. The safety housing based implant/medicament injecting system as claimed in any one of claim 1, wherein the cannula includes a fluid communicable connection with the plunger rod guide to receive the implant/medicament.

3. The safety housing based implant/medicament injecting system as claimed in claim 1, wherein the needle hub is coupled with an inner surface of the housing by a tongue and groove joint to arrest any rotational movement of the needle assembly with respect to the housing and allow only spring-biased forward and backward motion of the needle assembly within the housing.

4. The safety housing based implant/medicament injecting system as claimed in claim 1, wherein the positive lock includes;
   at least one opening or slot in the plunger externally at a front end of the plunger; and
   at least one cooperative protrusion on the second end of the safety clip configured to be detachably engaged with said at least one opening or slot in the plunger.

5. The safety housing based implant/medicament injecting system as claimed in claim 1, wherein the first end of the safety clip is coupled with the housing by a tongue and groove joint facilitating sliding of the safety clip through the housing;
- said first end of the safety clip is coupled with the label holder by a butt joint ensuring that pushing force applied on the plunger gets transferred to the needle assembly via the safety clip and enabling cooperative forward movement of the plunger and the needle assembly inside the housing; and
- said cooperative forward movement of the plunger and the needle assembly restricts plunger rod movement through the plunger rod guide and thus prevents movement of the implant/medicament independently with respect to the needle assembly during driving of the needle assembly.

6. The safety housing based implant/medicament injecting system as claimed in claim 5, wherein the seal releasing means is at the back end of the housing and includes:
- a mating protrusion on the housing which widens the second end of the safety clip when the second end interacts with said mating protrusion and detaches the positive lock; and
- a releasing gap on the tongue and groove joint on which the first end of the safety clip slides; wherein
- said seal releasing means facilitates removal of the safety clip and enables the plunger to move independently from the needle assembly so that further application of pushing force on the plunger in a forward direction in the housing independent of the needle assembly causes the plunger rod to move in the forward direction through the plunger rod guide and push the implant/medicament through the cannula into tissue.

7. The safety housing based implant/medicament injecting system as claimed in claim 1, wherein the first engagement means comprises a snap lock on the needle hub configured to engage with a cooperative locking portion in the housing cap when the cannula and a protective cap are completely ejected out from the housing after continued pushing force applied on the plunger causes the needle assembly to move towards a front end of the housing.

8. The safety housing based implant/medicament injecting system as claimed in claim 7, wherein the needle assembly is engaged with the housing as the snap lock on the needle hub gets locked with the cooperative locking portion in the housing cap, produces an audible click, compresses the spring so that forward and reverse movement of the needle assembly with respect to the housing is arrested, and facilitates piercing of the cannula, after removal of the protective cap, into a body, skin, or tissue.

9. The safety housing based implant/medicament injecting system as claimed in claim 7, wherein the first disengagement means includes a front end of the plunger and movement of the plunger towards the front end of the housing enables disengagement of the first engagement means;
- the disengagement of the first engagement means is achieved by sliding said front end of the plunger over the snap lock on the needle hub to compress the snap lock on the needle hub and disengage the needle assembly from the cooperative locking portion in the housing cap; and
- said disengaged needle assembly automatically retracts within the housing along with the cannula by expansion of the spring.

10. The safety housing based implant/medicament injecting system as claimed in claim 1, wherein the second engagement means includes a cooperative snap which resides within the housing to allow free movement of the needle assembly in a forward direction inside the housing and restrict accidental reverse motion of the needle assembly.

11. The safety housing based implant/medicament injecting system as claimed in claim 1, wherein the plunger includes a snap lock to secure the plunger within the housing after removal of the safety clip.

12. The safety housing based implant/medicament injecting system as claimed in claim 1, wherein a portion of the plunger inside said housing is retracted back with the needle assembly due to the plunger being engaged with the needle assembly.

13. The safety housing based implant/medicament injecting system as claimed in claim 1, wherein the second engagement means includes a locking means on the label holder to permanently couple the needle assembly in the housing after use.

* * * * *